US012420036B2

(12) United States Patent
Visco et al.

(10) Patent No.: US 12,420,036 B2
(45) Date of Patent: Sep. 23, 2025

(54) MULTI-PORT, HIGH-FLOW PNEUMOPERITONEUM AND SMOKE EVACUATION DISTRIBUTION DEVICES, SYSTEMS, AND METHODS

(71) Applicants: Duke University, Durham, NC (US); Zachary Visco, Chapel Hill, NC (US)

(72) Inventors: Anthony Visco, Durham, NC (US); Zachary Visco, Chapel Hill, NC (US)

(73) Assignees: Zachary Visco, Chapel Hill, NC (US); Duke University, Durham, NC (US)

( * ) Notice: Subject to any disclaimer, the term of this patent is extended or adjusted under 35 U.S.C. 154(b) by 0 days.

(21) Appl. No.: 18/292,474

(22) PCT Filed: Sep. 30, 2022

(86) PCT No.: PCT/US2022/077343
§ 371 (c)(1),
(2) Date: Jan. 26, 2024

(87) PCT Pub. No.: WO2023/056415
PCT Pub. Date: Apr. 6, 2023

(65) Prior Publication Data
US 2024/0261519 A1  Aug. 8, 2024

Related U.S. Application Data

(60) Provisional application No. 63/250,471, filed on Sep. 30, 2021.

(51) Int. Cl.
*A61M 13/00* (2006.01)
*A61M 1/00* (2006.01)
(Continued)

(52) U.S. Cl.
CPC .......... *A61M 13/006* (2014.02); *A61M 1/72* (2021.05); *A61M 39/12* (2013.01);
(Continued)

(58) Field of Classification Search
CPC ........ A61M 13/003; A61M 13/00–006; A61M 2202/0225; A61M 2205/12;
(Continued)

(56) References Cited

U.S. PATENT DOCUMENTS 1,669,333 A  *  5/1928  Gerber ................. D06B 23/00
                                                        220/534
3,858,572 A  *  1/1975  Binard ................. A61M 5/007
                                                        600/560
(Continued)

FOREIGN PATENT DOCUMENTS

| CN | 202844278 U | 4/2013 | |
|---|---|---|---|
| WO | WO-9813635 A1 * | 4/1998 | ............. E03C 1/023 |
| WO | WO-2011102669 A2 * | 8/2011 | ............. F16L 19/065 |

OTHER PUBLICATIONS

International Search Report and the Written Opinion of the International Searching Authority corresponding to International Patent Application No. PCT/US2022/077343 (8 pages) (mailed Dec. 19, 2022).

(Continued)

*Primary Examiner* — Bhisma Mehta
*Assistant Examiner* — Adam J. Cermak
(74) *Attorney, Agent, or Firm* — Myers Bigel, P.A.

(57) ABSTRACT

An insufflation system for creating a high-flow, constant pressure pneumoperitoneum, the system including: a gas flow distribution device including: a housing defining an insufflation chamber; an inlet port on the housing and configured to be connected to an insufflator to provide insufflation gas from the insufflator to the insufflation chamber; and a plurality of outlet ports on the housing configured to be connected to a plurality of trocars, each outlet port configured to be connected to a dedicated one of the plurality (Continued)

of trocars, to concurrently distribute the insufflation gas from the insufflation chamber to each of the plurality of trocars.

32 Claims, 27 Drawing Sheets

(51) Int. Cl.
  *A61M 39/12* (2006.01)
  *A61M 39/22* (2006.01)
(52) U.S. Cl.
  CPC . *A61M 2039/226* (2013.01); *A61M 2205/125* (2013.01); *A61M 2205/7536* (2013.01); *A61M 2210/1017* (2013.01)
(58) Field of Classification Search
  CPC .. A61M 2210/1017; A61M 2039/1038; B65D 90/0066; Y10T 137/87877
  USPC .................. 220/534, 544, 549; 137/883
  See application file for complete search history.

(56) References Cited

U.S. PATENT DOCUMENTS

| | | | | |
|---|---|---|---|---|
| 3,918,464 A * | 11/1975 | Kolodziej | ........... | A24F 1/30 131/179 |
| 4,096,868 A * | 6/1978 | Norman | ........... | A24F 1/30 131/194 |
| 4,253,247 A * | 3/1981 | Bergstrom | ........... | D21F 7/008 137/883 |
| 4,432,392 A * | 2/1984 | Paley | ........... | A61M 39/223 137/883 |
| 4,721,133 A * | 1/1988 | Sundblom | ........... | F16K 11/22 251/262 |
| 4,909,384 A * | 3/1990 | About | ........... | B65D 5/48024 206/77.1 |
| 5,020,469 A * | 6/1991 | Boissevain | ........... | D21F 7/008 118/118 |
| 5,109,822 A * | 5/1992 | Martin | ........... | F02D 41/3836 123/456 |
| 5,188,234 A * | 2/1993 | Fukuda | ........... | A45C 11/20 206/541 |
| 5,303,733 A * | 4/1994 | Nelson | ........... | G05D 16/0663 137/557 |
| 5,350,290 A * | 9/1994 | Honings | ........... | A21C 5/00 425/464 |
| 5,382,297 A | 1/1995 | Valentine et al. | | |
| 5,678,606 A * | 10/1997 | Redden | ........... | F16K 3/0218 251/114 |
| 5,937,907 A * | 8/1999 | Lee | ........... | F16L 41/03 138/42 |
| 6,299,592 B1 * | 10/2001 | Zander | ........... | A61M 13/003 600/560 |
| 6,325,103 B1 * | 12/2001 | Cox | ........... | F16K 11/20 137/883 |
| 6,340,034 B1 * | 1/2002 | Arnott | ........... | F16K 27/003 137/550 |
| 6,736,155 B1 * | 5/2004 | Johnson | ........... | F16N 37/00 137/263 |
| 7,654,975 B2 * | 2/2010 | Mantell | ........... | A61M 13/003 604/26 |
| 7,704,223 B2 * | 4/2010 | Mantell | ........... | A61M 13/003 604/24 |
| 7,981,072 B2 * | 7/2011 | Uesugi | ........... | A61M 13/003 604/23 |
| 7,988,656 B2 * | 8/2011 | Uesugi | ........... | A61B 1/015 604/23 |
| 8,840,580 B2 * | 9/2014 | Uesugi | ........... | A61B 50/10 600/560 |
| 8,893,915 B2 * | 11/2014 | Vargas | ........... | B65D 25/04 220/544 |
| 8,920,431 B2 | 12/2014 | Shibley et al. | | |
| 9,004,306 B2 * | 4/2015 | Platt | ........... | B09B 3/80 220/254.1 |
| 9,259,541 B2 * | 2/2016 | Temple | ........... | A61M 13/006 |
| 10,159,809 B2 | 12/2018 | Mastri et al. | | |
| 10,757,968 B1 * | 9/2020 | Siefert | ........... | A24F 1/30 |
| 10,881,135 B1 * | 1/2021 | Magnuson | ........... | A61M 15/0006 |
| 11,065,035 B2 * | 7/2021 | Silver | ........... | A61B 17/3423 |
| 2001/0000262 A1 * | 4/2001 | McEwen | ........... | A61H 9/0078 601/11 |
| 2002/0074047 A1 * | 6/2002 | Gagnon | ........... | H01M 8/04089 137/883 |
| 2002/0096525 A1 * | 7/2002 | Bertoldo | ........... | B65D 25/06 220/570 |
| 2004/0153027 A1 * | 8/2004 | Mantell | ........... | A61M 16/202 604/23 |
| 2005/0015043 A1 * | 1/2005 | Stubbs | ........... | A61B 17/3421 604/164.01 |
| 2005/0171466 A1 * | 8/2005 | Diemunsch | ........... | A61M 11/042 604/26 |
| 2006/0058617 A1 * | 3/2006 | Sano | ........... | A61B 1/3132 600/407 |
| 2006/0129087 A1 * | 6/2006 | Uesugi | ........... | A61M 13/003 604/118 |
| 2006/0217683 A1 * | 9/2006 | Patania | ........... | A61M 39/10 604/533 |
| 2007/0163585 A1 * | 7/2007 | Uesugi | ........... | A61M 13/003 128/204.18 |
| 2007/0255165 A1 * | 11/2007 | Uesugi | ........... | A61B 1/015 600/560 |
| 2010/0101186 A1 * | 4/2010 | Cronin | ........... | B65D 83/0083 53/436 |
| 2010/0114011 A1 * | 5/2010 | Herrmann | ........... | A61M 13/003 137/100 |
| 2010/0212678 A1 * | 8/2010 | Bishara | ........... | A24F 1/30 131/173 |
| 2011/0030678 A1 | 2/2011 | Power et al. | | |
| 2012/0150101 A1 | 6/2012 | Stearns et al. | | |
| 2012/0310147 A1 * | 12/2012 | Poll | ........... | A61B 17/3421 604/164.11 |
| 2014/0074015 A1 | 3/2014 | Mastri et al. | | |
| 2014/0309583 A1 | 10/2014 | Stearns et al. | | |
| 2015/0153746 A1 * | 6/2015 | Lee | ........... | B67D 7/78 137/883 |
| 2015/0250958 A1 * | 9/2015 | Hayashi | ........... | A61M 39/22 604/26 |
| 2016/0066619 A1 * | 3/2016 | Di Carlo | ........... | A24F 40/50 131/329 |
| 2016/0106934 A1 * | 4/2016 | Hiraga | ........... | A61B 1/3132 604/26 |
| 2016/0317081 A1 * | 11/2016 | Huang | ........... | A61B 5/03 |
| 2017/0049473 A1 * | 2/2017 | Amson | ........... | A61M 13/006 |
| 2017/0087311 A1 * | 3/2017 | Sias | ........... | A61B 17/3423 |
| 2020/0268989 A1 | 8/2020 | Radl et al. | | |
| 2020/0316320 A1 * | 10/2020 | Nelson | ........... | A61M 13/003 |
| 2020/0367552 A1 * | 11/2020 | Delgado | ........... | A24F 1/30 |
| 2021/0001059 A1 * | 1/2021 | Kasuya | ........... | A61M 13/003 |
| 2021/0145045 A1 * | 5/2021 | Steiner | ........... | A24F 1/30 |
| 2021/0251655 A1 * | 8/2021 | Litke | ........... | A61B 34/35 |
| 2022/0105283 A1 * | 4/2022 | Litke | ........... | A61M 13/003 |
| 2022/0152321 A1 * | 5/2022 | Haber | ........... | B01D 46/46 |
| 2022/0203048 A1 * | 6/2022 | Litke | ........... | A61M 39/10 |
| 2022/0233790 A1 * | 7/2022 | Koltz, Jr. | ........... | A61L 9/20 |
| 2022/0233791 A1 * | 7/2022 | Koltz, Jr | ........... | A61M 13/006 |
| 2022/0233792 A1 * | 7/2022 | Koltz, Jr. | ........... | A61M 16/0066 |
| 2022/0233793 A1 * | 7/2022 | Koltz, Jr. | ........... | A61M 13/006 |
| 2022/0233794 A1 * | 7/2022 | Koltz, Jr. | ........... | A61M 13/00 |
| 2022/0280736 A1 * | 9/2022 | Spence | ........... | A61M 16/024 |
| 2023/0025578 A1 * | 1/2023 | Whyte | ........... | A24F 1/30 |
| 2023/0049600 A1 * | 2/2023 | Langen | ........... | A61M 13/003 |
| 2023/0066076 A1 * | 3/2023 | O'Dea | ........... | A41D 13/1107 |

(56) References Cited

U.S. PATENT DOCUMENTS

2023/0364358 A1* 11/2023 Foley ................. A61B 17/3423
2024/0001053 A1* 1/2024 Henley .................... A61L 9/22

OTHER PUBLICATIONS

LSI Solutions PNEUMOSTOP® DEVICE Technology Guide Product Insert, https://www.lsisolutions.com/media/apps/general/product_resource_inside_us/PneumoStopProduct_Insert.pdf?v=1594157353 (2 pages) (2019).
Cassata, et al., "OneShot-M: A New Device for Close Laparoscopy Pneumoperitoneum", Surgical Innovation, 2018, 25(6):1-8.
Choudhary, et al., "Simple Device Design for Plume Management after Pneumoperitoneum in Laparoscopy in COVID-19 Outbreak", Indian Journal of Surgery, 2020, 82(3):274-275.
Communication with Supplementary European Search Report, EP Application No., 22877607.6, Mar. 17, 2025, 13 pp.

* cited by examiner

MULTI-PORT, HIGH-FLOW PNEUMOPERITONEUM AND SMOKE EVACUATION DISTRIBUTION DEVICES, SYSTEMS, AND METHODS

RELATED APPLICATIONS

This application is a 35 U.S.C. § 371 national phase entry of International Application No. PCT/US2022/077343, filed Sep. 30, 2022, which application claims priority from U.S. Provisional Patent Application Ser. No. 63/250,471, filed Sep. 30, 2021, the disclosure of which is incorporated by reference in its entirety.

BACKGROUND

Laparoscopic surgery is often aided by pneumoperitoneum, or the insufflation of a gas into the body cavity to create a surgical space. While pneumoperitoneum is essential to visibility during surgery, there are some challenges associated with creating and maintaining gas pressure. Pneumoperitoneum is typically created using a single inflow tubing containing carbon dioxide connected to a single laparoscopic trocar using luer lock connections. The available internal capacity of the trocar to carry high-flow gas is further significantly reduced by the introduction of surgical tools (e.g., a laparoscopic or robotic instrument, suction device, camera, etc.) into the trocar as these devices take up the majority of the available internal trocar volume. One current solution is a valveless trocar system that uses outer channels to carry gases around a central trocar sheath. However, this significantly increases the overall size of the valveless trocar, requiring larger skin and fascial incisions that have been associated with an increased risk of postoperative hernia formation. Another drawback of pneumoperitoneum-assisted laparoscopy is the loss of pneumoperitoneum that can occur, particularly during suctioning or during a total hysterectomy when an incision is made in the vagina allowing the rapid escape of gas. This is particularly problematic during robotic surgery, where the trocars are attached to fixed robotic arms. Pressure loss can cause the abdominal wall to drop away, resulting in the trocars becoming malpositioned. In light of these and other challenges, there is an ongoing need for improved insufflation systems and methods.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides all that is described and illustrated herein.

Some embodiments of the present disclosure are directed to an insufflation system for creating a high-flow, constant or variable pressure pneumoperitoneum, the system including a gas flow distribution device. The gas flow distribution device includes: a housing defining an insufflation chamber; an inlet port on the housing and configured to be connected to an insufflator to provide insufflation gas from the insufflator to the insufflation chamber; and a plurality of outlet ports on the housing configured to be connected to a plurality of insufflation trocars, each outlet port configured to be connected to a dedicated one of the plurality of trocars, to concurrently distribute the insufflation gas from the insufflation chamber to each of the plurality of trocars.

In some embodiments, the inlet port includes a barb configured to directly engage an inner surface of tubing connected thereto. The inlet port may include a luer lock connection configured to receive a luer lock fitting.

In some embodiments, each outlet port includes a barb configured to directly engage an inner surface of tubing connected thereto. In some embodiments, each outlet port includes a luer lock connection configured to receive a luer lock fitting.

In some embodiments, the system further includes a plurality of outlet tubes, each outlet tube including a first end and a second opposite end, the first end of each outlet tube configured to be connected to a corresponding one of the outlet ports, the second end of each outlet tube configured to be connected to the dedicated trocar. The first end of each outlet tube may be pressure fit to a corresponding one of the outlet ports such that an inner surface of the outlet tube directly engages a barb on an outer surface of the outlet port. The system may further include a luer lock fitting at the second end of each of the outlet tubes.

In some embodiments, the system further includes a reservoir in a top of the housing that is sized and configured to receive and hold a sponge comprising surfactant to reduce fogging on a laparoscopic lens. In some embodiments, the inlet port and the plurality of outlet ports are on the top of the housing and surround the reservoir.

In some embodiments, the housing is circular in shape.

In some embodiments, the housing is polygonal in shape.

In some embodiments, the housing has a shape of a torus optionally with a flat bottom surface.

In some embodiments, the housing includes a bottom portion and a top portion that are configured to be coupled together. The bottom portion and the top portion may be configured to be coupled with an interference fit. The bottom portion and the top portion may be configured to be threadingly engaged. The bottom portion may include threads on an outer surface thereof and the top portion may include threads on an inner surface thereof.

In some embodiments, the housing further defines an exhaust chamber, and the insufflation system further includes: at least one exhaust inlet port on the housing and configured to be connected to an exhaust trocar to provide suction and/or evacuate smoke from the exhaust trocar to the exhaust chamber; and an exhaust outlet port on the housing and configured to be connected to an exhaust device to provide exhaust from the exhaust chamber to the exhaust device.

In some embodiments, the housing includes a partition that isolates the insufflation chamber and the exhaust chamber from one another.

In some embodiments, the partition includes an insert configured to be received through at least one slot in a side wall of the housing. The at least one slot may include first and second slots, the device further includes a flex port between the first and second slots, and the insert is configured to selectively be received (i) through the first slot such that the at least one exhaust outlet port is in fluid communication with the exhaust chamber and the flex port is in fluid communication with the insufflation chamber and (ii) through the second slot such that the at least one exhaust outlet port and the flex port are in fluid communication with the exhaust chamber. The insert may be a first insert, and the insufflation system may further include a second insert configured to be received in and plug the first or second slot that is not holding the first insert.

In some embodiments, the system further includes at least one (exhaust) inlet tube each including a first end and a second opposite end, the first end of each inlet tube configured to be connected to a corresponding one of the at least one inlet port, the second end of each inlet tube configured to be connected to a dedicated exhaust trocar. The first end of each inlet tube may be pressure fit to a corresponding one of the at least one inlet port such that an inner diameter of the inlet tube directly engages a barb on an outer surface of the inlet port. The system may further include a luer lock fitting at the second end of each inlet tube.

In some embodiments, the gas flow distribution device is a first gas flow distribution device, the housing is a first housing, and the system further includes a second gas flow distribution device. The second gas flow distribution device includes: a second housing defining an exhaust chamber; at least one exhaust inlet port on the second housing and configured to be connected to an exhaust trocar to provide suction and/or evacuate smoke from the trocar to the exhaust chamber; and an exhaust outlet port on the second housing and configured to be connected to an exhaust device to provide exhaust from the exhaust chamber to the exhaust device.

In some embodiments, the system further includes at least one (exhaust) inlet tube each including a first end and a second opposite end, the first end of each inlet tube configured to be connected to a corresponding one of the at least one inlet port, the second end of each inlet tube configured to be connected to a dedicated exhaust trocar. The first end of each inlet tube may be pressure fit to a corresponding one of the at least one inlet port such that an inner diameter of the inlet tube directly engages a barb on an outer surface of the inlet port. The system may further include a luer lock fitting at the second end of each inlet tube.

In some embodiments, the system further includes a suction system including a suction line configured to connect at least one of the plurality of insufflation trocars or the exhaust trocar and the exhaust device or a separate suction device, the system further including at least one valve in the suction line configured to close a smoke evacuation line comprising the exhaust outlet port when the at least one valve is open to the exhaust device or the separate suction device, and to open the smoke evacuation line when the at least one valve is closed to the exhaust device or the separate suction device.

Some other embodiments of the present disclosure are directed to a method for creating a high-flow, constant or variable pressure pneumoperitoneum, the method including inducing a pneumoperitoneum in a patient including: providing a device including a housing defining an insufflation chamber, an inlet port fluidly connected to the insufflation chamber, and a plurality of outlet ports fluidly connected to the insufflation chamber; flowing gas from an insufflator through the inlet port and into the insufflation chamber; and flowing the gas from the insufflation chamber concurrently through each of the plurality of outlet ports to a plurality of trocars in the patient, wherein each outlet port is fluidly connected to a dedicated one of the plurality of trocars.

In some embodiments, the method further includes, before inducing the pneumoperitoneum in the patient, for each outlet port, connecting a first end of an outlet tube to the outlet port and connecting a second end of the outlet tube to the dedicated one of the plurality of trocars. Connecting the second end of the outlet tube to the dedicated one of the plurality of trocars may include connecting the second end of the outlet tube to the dedicated one of the plurality of trocars using a luer lock connection. Connecting a first end of an outlet tube to the outlet port may include connecting the first end of the outlet tube to the outlet port using a pressure fit such that an inner surface of the outlet tube directly engages a barb on the outlet port.

In some embodiments, the method includes, before inducing a pneumoperitoneum in a patient, connecting an inlet tube extending from the insufflator to the inlet port using a pressure fit such that an inner surface of the inlet tube directly engages a barb on the inlet port.

In some embodiments, the method further includes evacuating smoke from an abdomen of the patient while inducing the pneumoperitoneum in the patient.

In some embodiments, the method further includes providing an exhaust chamber, an exhaust inlet port fluidly connected to the exhaust chamber, and an exhaust outlet port fluidly connected to the exhaust chamber, and evacuating smoke from the abdomen of the patient includes: flowing smoke from an exhaust trocar through the exhaust inlet port and into the exhaust chamber; and flowing the smoke from the exhaust chamber through the exhaust outlet port and to a suction device. The exhaust inlet port may include first and second exhaust inlet ports, and evacuating smoke from the abdomen of the patient may include: flowing first smoke from a first exhaust trocar through the first exhaust inlet port and into the exhaust chamber; concurrently with flowing the first smoke, flowing second smoke from a second exhaust trocar through the second exhaust inlet port and into the exhaust chamber; and flowing the first and second smoke from the exhaust chamber through the exhaust outlet port and to a suction device.

In some embodiments, the device includes the exhaust chamber.

In some embodiments, the device is a first device, and the exhaust chamber is defined by a housing of a second device.

In some embodiments, the method further includes suctioning fluid from the abdomen of the patient. The method may further include halting evacuating smoke from the abdomen of the patient before suctioning fluid from the abdomen of the patient, and resuming evacuating smoke from the abdomen of the patient after suctioning fluid from the abdomen of the patient.

In some embodiments, halting evacuating smoke from the abdomen of the patient includes closing at least one valve in a smoke evacuation line in response to opening at least one valve in a suction line, and resuming evacuating smoke from the abdomen of the patient includes opening at least one valve in the smoke evacuation line in response to closing at least one valve in the suction line.

Some other embodiments of the present disclosure are directed to an insufflation system for creating a high-flow, constant or variable pressure pneumoperitoneum. The system includes: an insufflator; first and second trocars in an abdomen of a patient; and a gas flow distribution device. The gas flow distribution device includes: a housing defining an insufflation chamber; an inlet port on the housing connected to the insufflator to provide insufflation gas from the insufflator to the insufflation chamber; and first and second outlet ports on the housing, the first outlet port connected to the first trocar and the second outlet port connected to the second trocar, to concurrently distribute the insufflation gas from the insufflation chamber to each of the first and second trocars.

The accompanying Figures and examples are provided by way of illustration and not by way of limitation. The foregoing aspects and other features of the disclosure are explained in the following description, taken in connection with the accompanying example figures relating to one or more embodiments.

DETAILED DESCRIPTION

Figure 1:
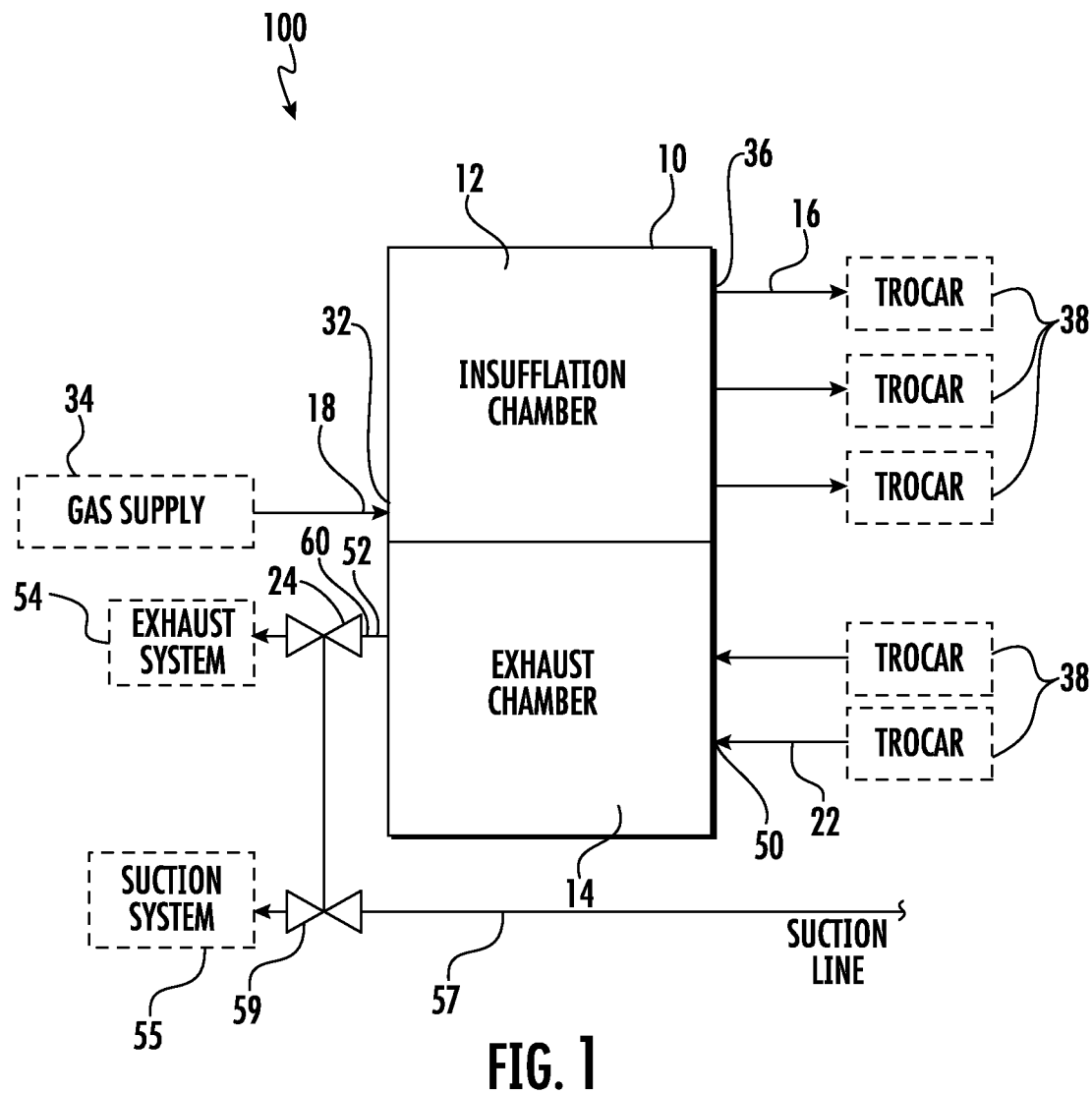
FIG. 1 is a schematic diagram of an insufflation system according to some embodiments.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human who is undergoing an insufflation procedure using a system or method as prescribed herein.

Unless otherwise defined, all technical terms used herein have the same meaning as commonly understood by one of ordinary skill in the art to which this disclosure belongs. Like numbers refer to like elements throughout.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

During a laparoscopic procedure, pneumoperitoneum is induced in the patient. Insufflation gas, typically carbon dioxide ($CO_2$), is provided by a regulated source unit and insufflated into a patient via trocars. These source units can supply a gas flow of approximately 40-45 L/min at a pressure of about 15 mm Hg. However, this flow profile cannot be achieved at the body cavity entry point due to cumulative line restrictions. For example, the large capacity tubing attached to the source unit is often reduced down to fit a conventional luer lock fitting, where it is connected to a single laparoscopic trocar. Gas flow is then further restricted when a laparoscopic instrument is inserted through the trocar, thus occupying the volume within the trocar. As a result, gas flow is significantly diminished by the time it reaches the patient. This can cause instability of the pneumoperitoneum due to the small difference in relative pressure between the supply and exhaust. This is particularly challenging during suctioning (e.g., removal of bio matter or fluids from the surgical area) and/or smoke removal (e.g., smoke resulting from a coagulation procedure). When suctioning and smoke evacuation are combined together, the risk increases for a net negative pressure to develop and drop pneumoperitoneum. When this happens, the trocars can become dislodged, or the body cavity can shift, causing internal structures to obstruct the surgical view.

The present disclosure addresses these and other challenges by providing an insufflation system that is capable of providing a high-flow, constant or variable pressure pneumoperitoneum. The disclosed system overcomes the inadequate bore size of existing standard trocars and obviates the need for larger trocars, thus increasing reliability while minimizing incision size.

FIGS. 1-4 illustrate examples of the disclosed system. FIG. 1 is a schematic diagram of an example embodiment of an insufflation system 100. Insufflation system 100 includes a gas flow (pneumoperitoneum) distribution element or device 10, which comprises two chambers and multiple inflow/outflow ports. The first chamber is a gas supply (e.g., $CO_2$) or insufflation chamber 12, and the second chamber is an optional smoke evacuation or exhaust chamber 14. Insufflation chamber 12 connects to an insufflation gas supply and acts as a manifold to distribute the gas to multiple trocars. These trocars can advantageously be existing trocars that are inserted in the patient and intended to be used as surgical ports. Optionally, insufflation chamber 12 can also distribute gas to trocars dedicated to creating pneumoperitoneum.

Insufflation chamber 12 is fluidly connected to the trocars is via tubing 16 and to an insufflation source unit via inlet tubing 18. Gas enters insufflation chamber 12 through an inlet port and exits to the trocars via multiple exit or outlet ports. The inlet and exit ports can optionally have features to improve gas flow and minimize losses, such as smooth surfaces and contoured edges. The tubing connections at distribution element 10 can be any suitable type of connector, such as a push-on tubing fitting or luer fittings. The opposite end of tubing 16 can also be any suitable connector, such as a luer fitting for connecting with a luer connection commonly found on trocars. In the example embodiment of FIG. 1, insufflation chamber 12 is shown with three exit ports; other numbers of exit ports are possible and within the scope of the disclosure. Unused ports can be capped to prevent gas leakage, either at the distribution port or at the end of a tubing 16. Because inlet tubing 18 is separate from trocar tubing 16, inlet tubing 18 can advantageously be a larger size without detriment to the patient. Multiple fluid paths provide a higher gas flow rate to the patient than can be achieved through a single trocar of the same size.

The presently disclosed system can be used with trocars of any size. In particular, the disclosed system advantageously facilitates high-flow insufflation at variable pressures through surgical trocars having an outside diameter of approximately 8 mm or less. Unlike large trocars (e.g., >10 mm outside diameter), which require large fascial incisions associated with a higher risk of bowel herniation, smaller trocars have correspondingly smaller incisions, which do not require closure and which heal more quickly. Further, laparoscopic surgery typically uses 3-5 trocars, only one of which can be accessed using current insufflation solutions. For example, a typical robotic surgery often has 3-4 robotic trocars in place (e.g., a camera port and 2-3 robotic arm instrument ports) plus an assistant trocar port for suctioning, introduction of suture material, tissue removal devices, etc. With the presently disclosed system, a user can customize the number and location of insufflation and/or exhaust locations to maintain a pressure and flow rate similar to that of the source unit.

Exhaust chamber 14 is fluidly isolated from insufflation chamber 12. Exhaust chamber 14 acts as a "pass through" for the smoke evacuation plume and exhaust gas, and it can be connected to the patient via tubing 22. Exhaust chamber 14 can be attached to two or more trocars allowing for more rapid removal of smoke and plume. For example, tubing 22 can be attached to an "exhaust trocar" via a luer or other suitable connector. Having smoke evacuation exiting from a trocar distinct from insufflation creates gas movement and flow within the surgical cavity that improves vision by more efficiently distributing and removing smoke plume. Optionally, exhaust chamber 14 can include a filter (not shown), which can be user accessible for disposal and replacement. The filter can be, for example, a HEPA filter designed to scrub toxins from the exhaust.

By co-locating the insufflation and exhaust chambers within the distribution device 10, the system is conveniently compact and simple to set up. However, other configurations are also possible. In some embodiments, exhaust chamber 14 is a separate component, or it is eliminated altogether. In some embodiments, system 100 comprises an optional valve 24 that can be configured to temporarily stop smoke evacuation while suction is activated.

More particularly, it is possible for insufflation system 100 to be functionally combined with an existing suctioning and/or exhaust system. Valve 24 can be configured in such a manner that suctioning and exhaust can use the same negative pressure source. For example, valve 24 can be a switching or 3-way valve that allows only the suctioning or the exhaust to be operated at a given time, or it can be a metering valve that limits the pressure. Alternately, valve 24 can simply be a manual valve operated by the surgical team to control the exhaust rate. Often, when smoke evacuation is functioning and suctioning of fluid is performed, gas is also suctioned by the laparoscopic suctioning device when the holes on the distal end of the suction apparatus are not maintained fully below the level of the fluid meniscus. Simultaneous smoke evacuation and gas suctioning from the suction device results in rapid decompression of the gas in the body chamber and a rapid drop in insufflation pressure. This results is organs such as bowel to fall into the operative field or mispositioning of laparoscopic or robotic trocars resulting in patient safety concerns or prolonged operative time associated with repositioning.

Figure 2A:
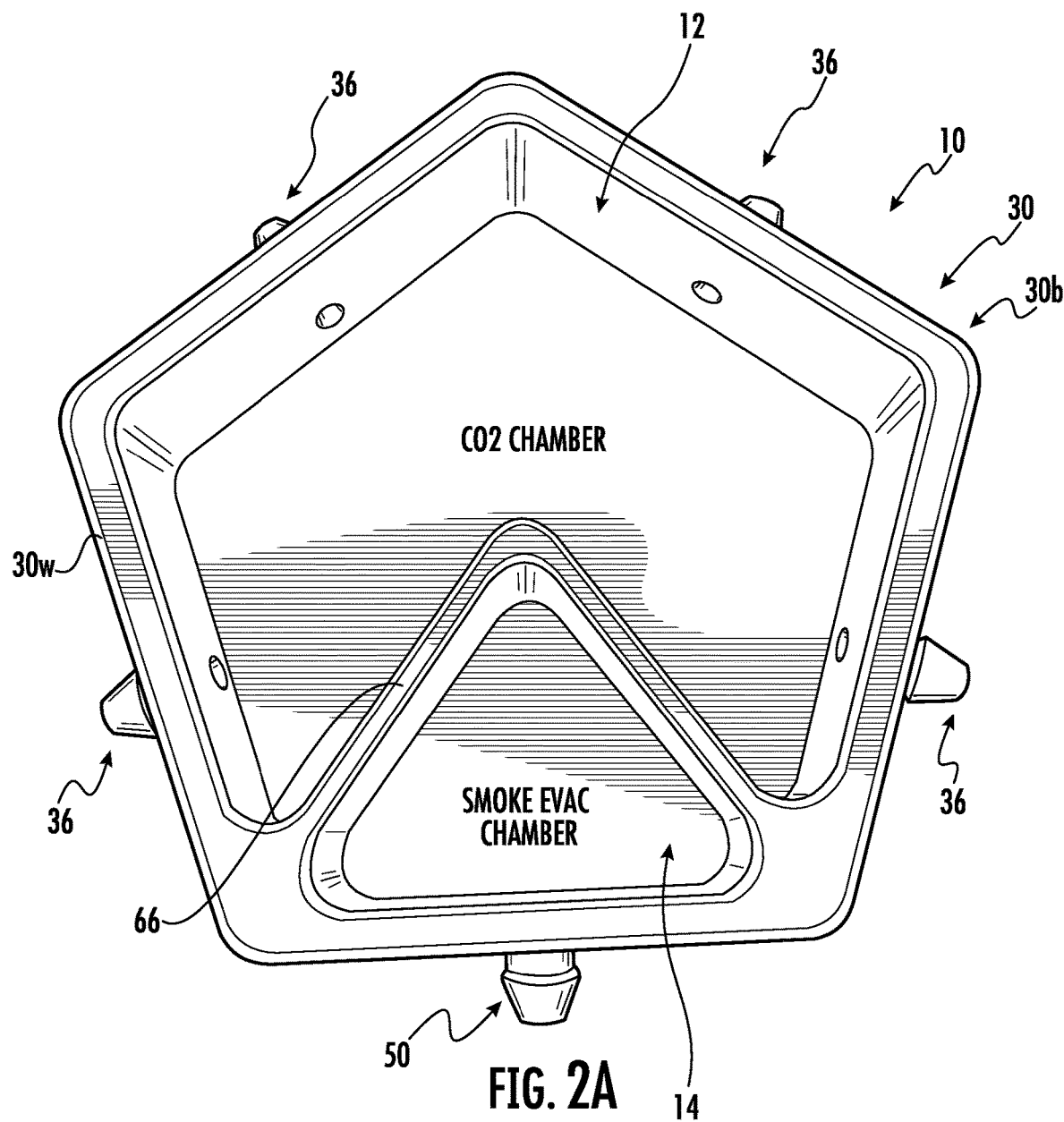
FIG. 2A is a top perspective view of a bottom portion of a housing of a gas flow distribution device used in the system of FIG. 1.
Figure 2B:
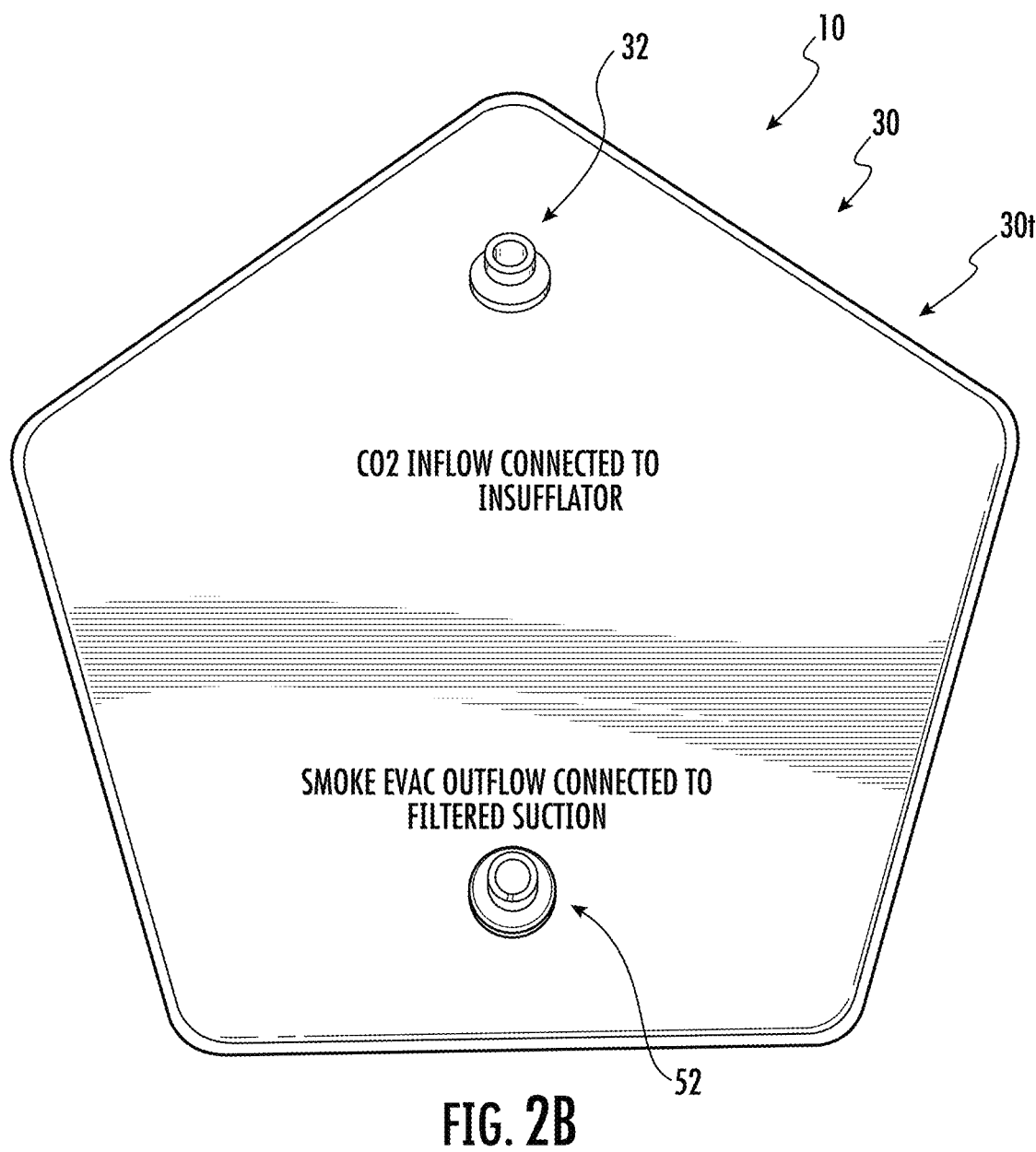
FIG. 2B is a top perspective view of a top portion of a housing of a gas flow distribution device used in the system of FIG. 1.
Figure 2C:
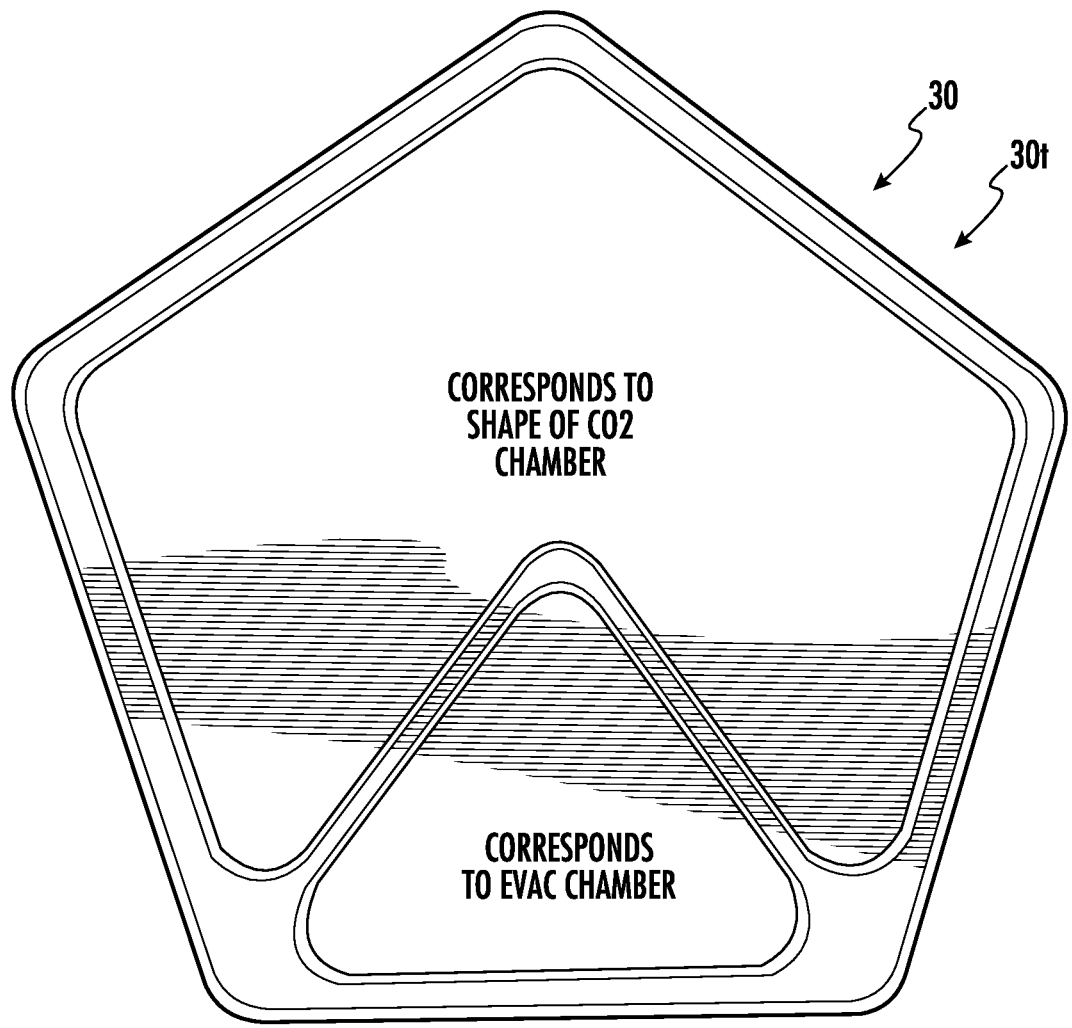
FIG. 2C is a bottom perspective view of the top portion of the housing of FIG. 2B.

FIGS. 2A-2C illustrate an example distribution device 10. The various inlet and outlet ports can be arranged in any suitable configuration, and the chambers can be of any suitable shape. In the example embodiment of FIG. 2, distribution device 10 has a pentagonal shape with four outlet ports. The inlet to insufflation chamber 12 is disposed on a planar "top" surface and the trocar outlets are disposed on edge faces. In this example, distribution device 10 is formed in two pieces that can be assembled in a suitable fashion, optionally with a gasket and fastening features (not shown). Alternately, distribution device 10 can be formed as a monolithic part using additive manufacturing, for example. In a non-limiting example embodiment, the distribution chamber can be approximately 4-6 inches in width and 2-4 inches in height. In a non-limiting example embodiment, the distribution device 10 weighs less than 100 grams.

Figure 3A:
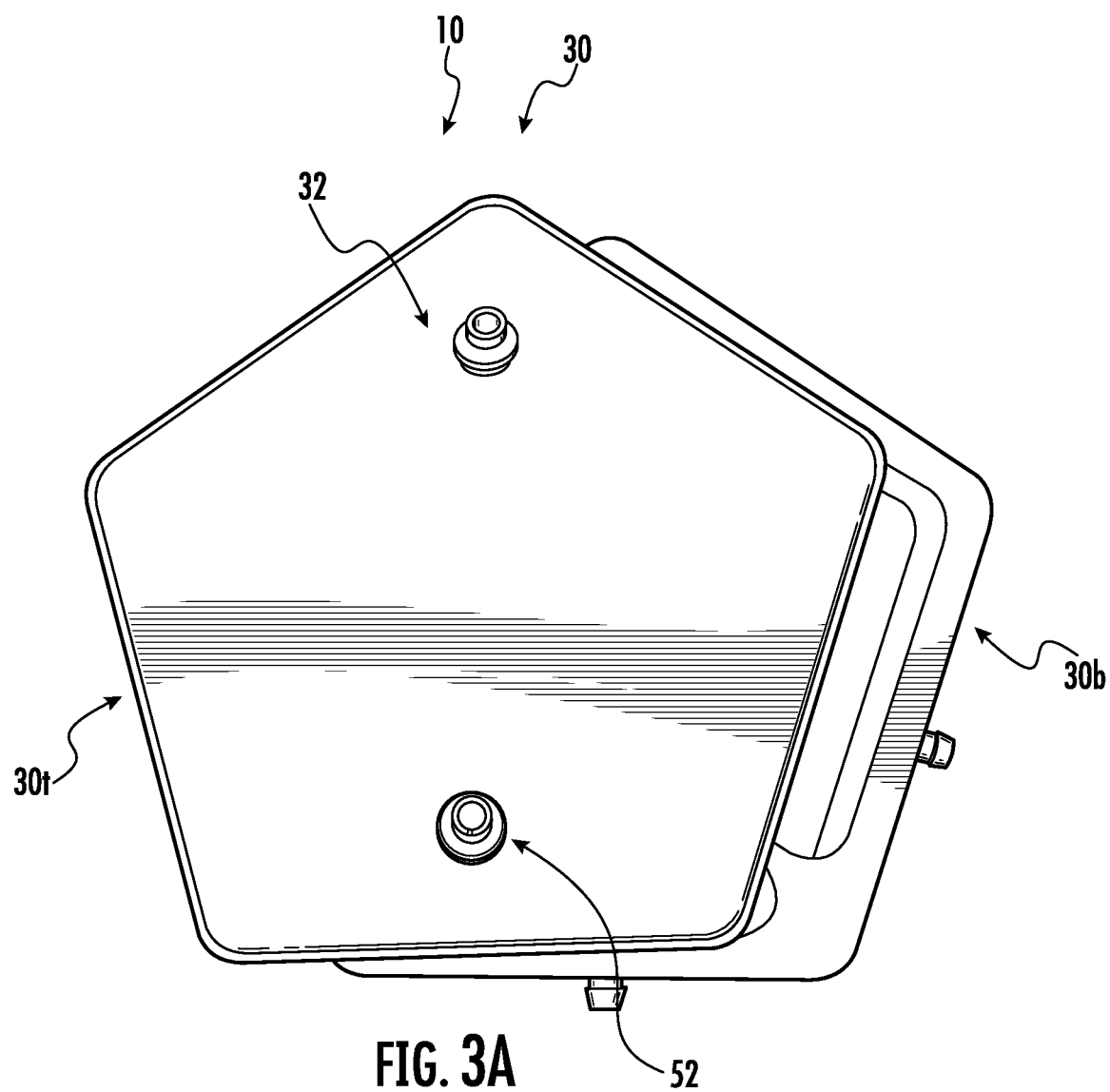
FIG. 3A is a partially assembled view of a gas flow distribution device including a housing including top and bottom portions.
Figure 3B:
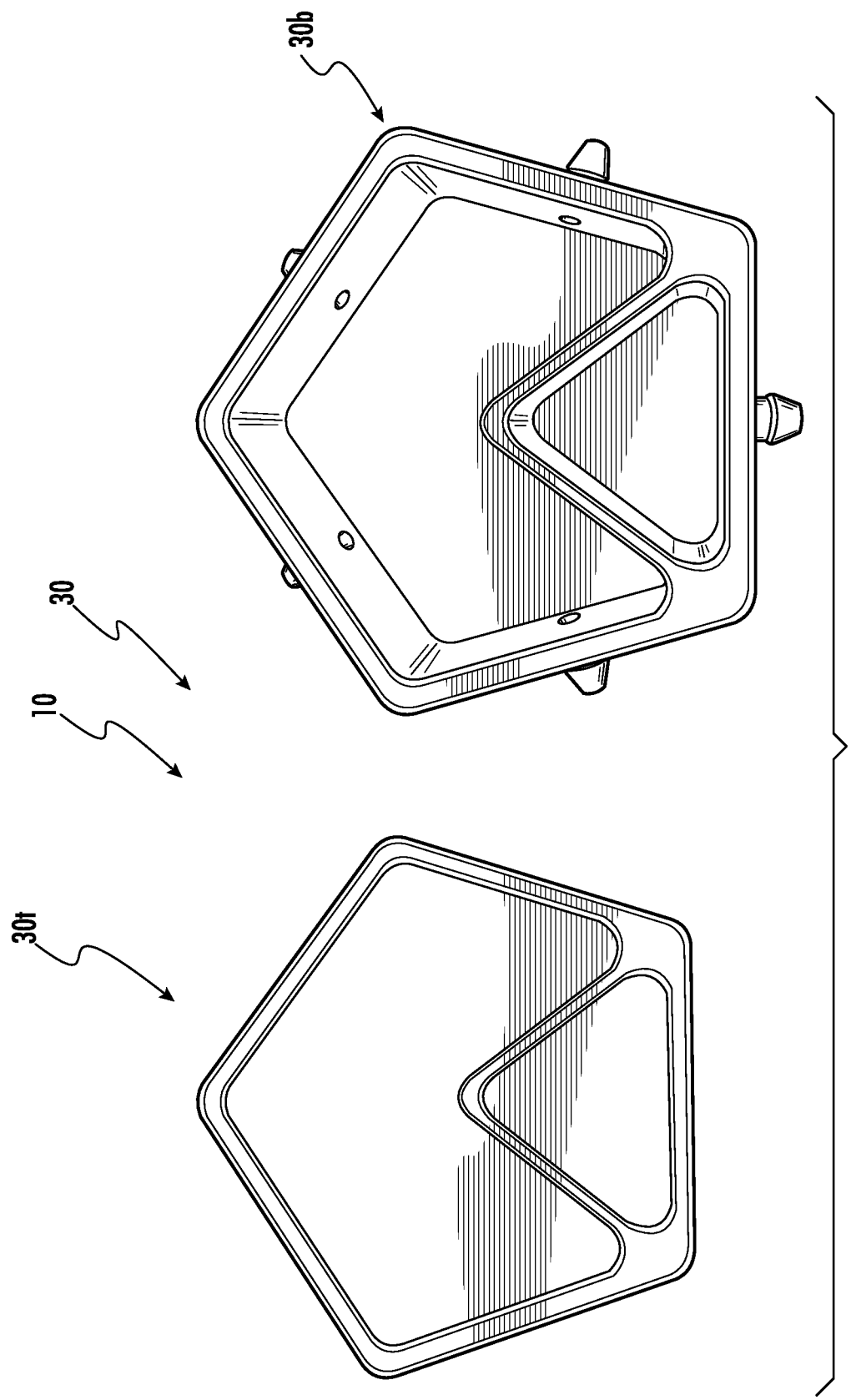
FIG. 3B is a side-by-side view of the top and bottom portions of the housing of FIG. 3A.
Figure 3C:
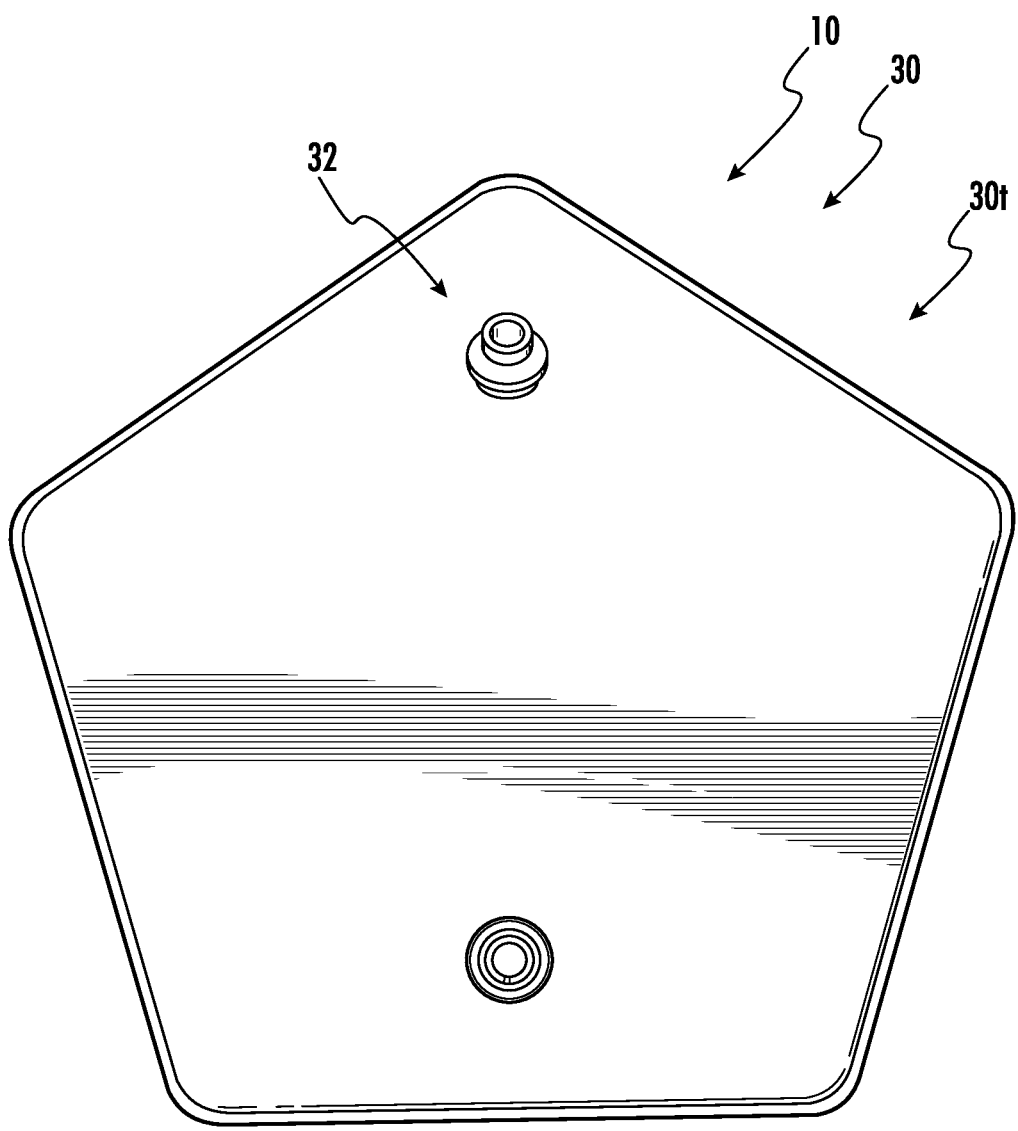
FIG. 3C is a top view of the top portion of the housing of FIG. 3A.
Figure 3D:
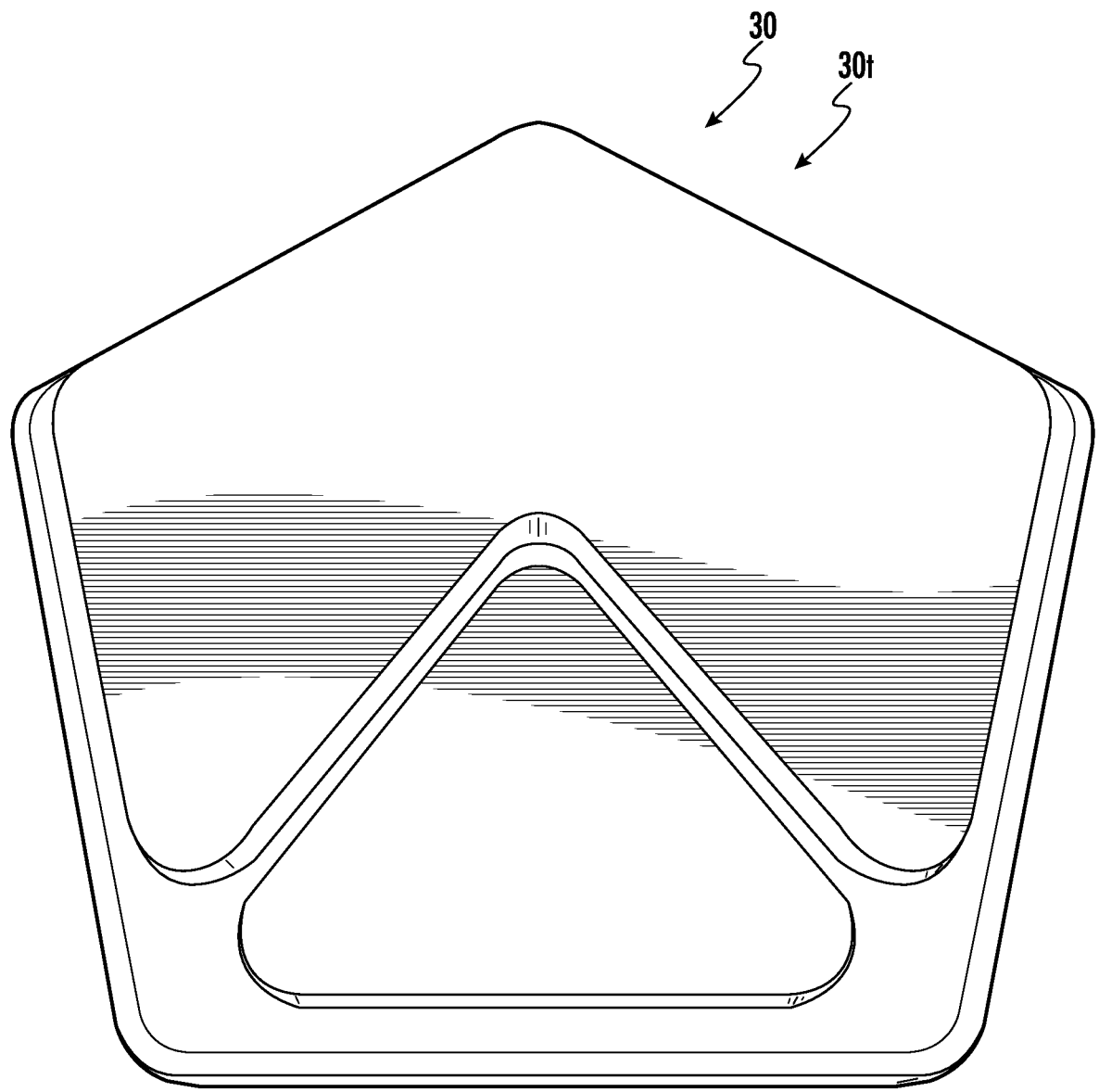
FIG. 3D is a bottom perspective view of the top portion of the housing of FIG. 3A.
Figure 3E:
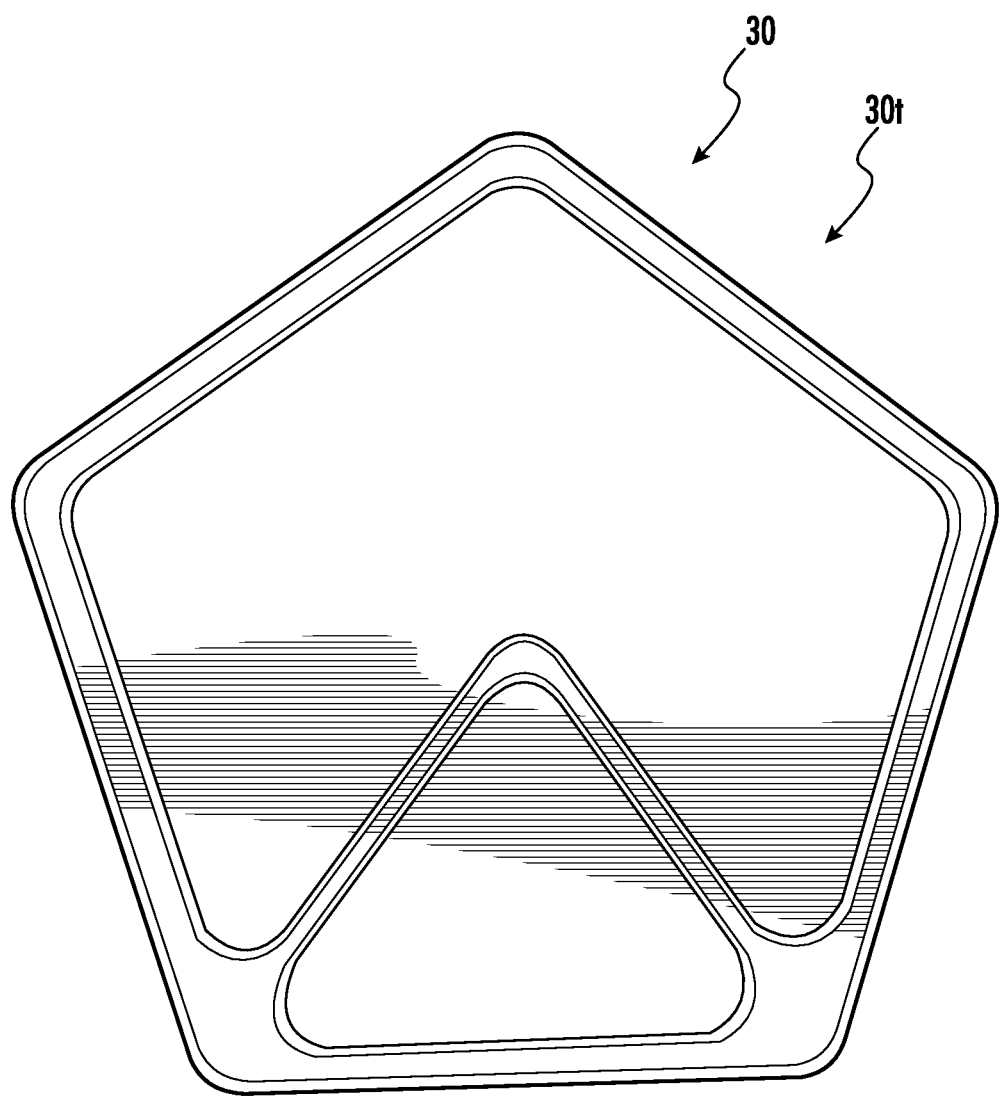
FIG. 3E is a bottom view of the top portion of the housing of FIG. 3A.
Figure 3F:
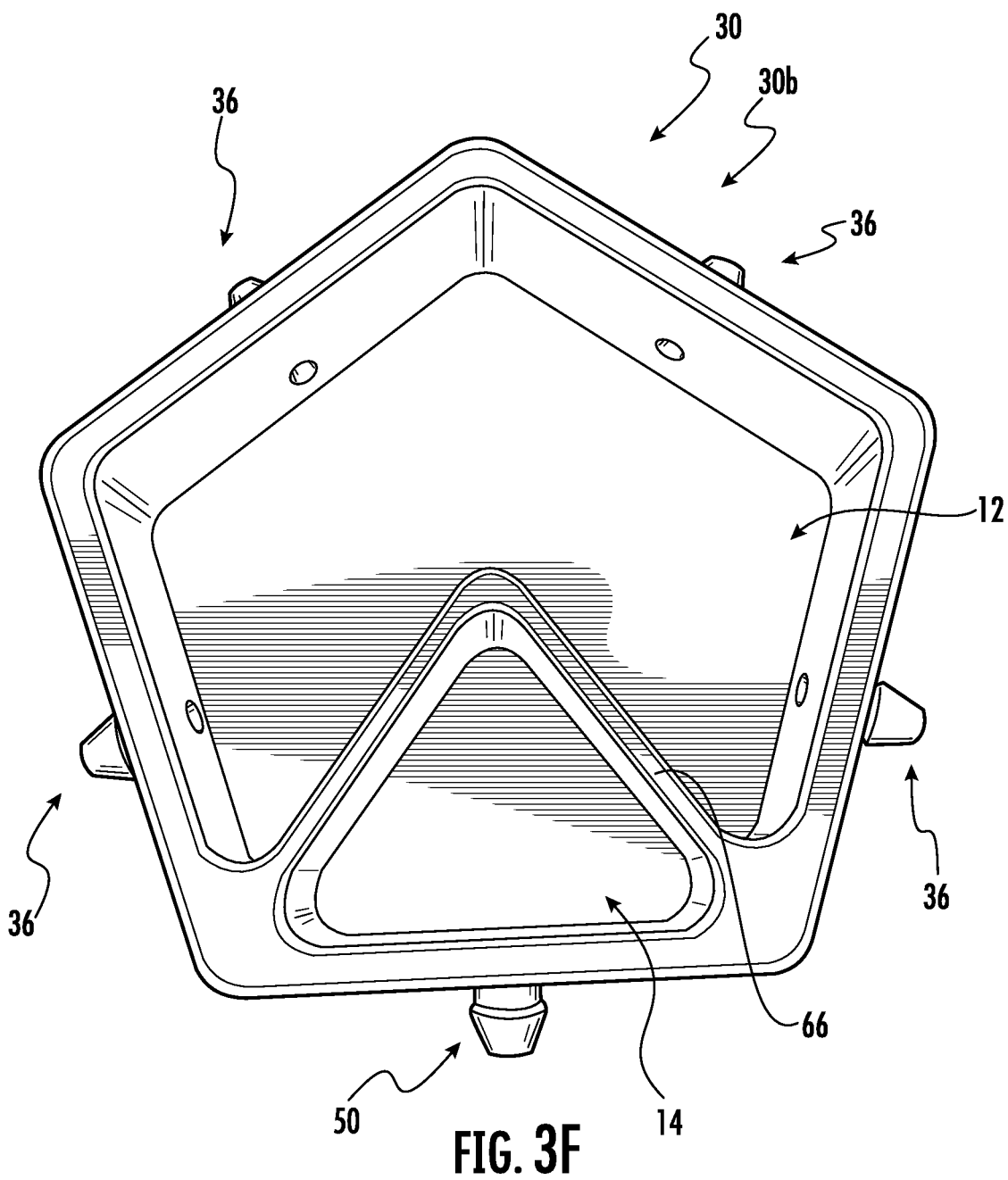
FIG. 3F is a top perspective view of the bottom portion of the housing of FIG. 3A.
Figure 4:
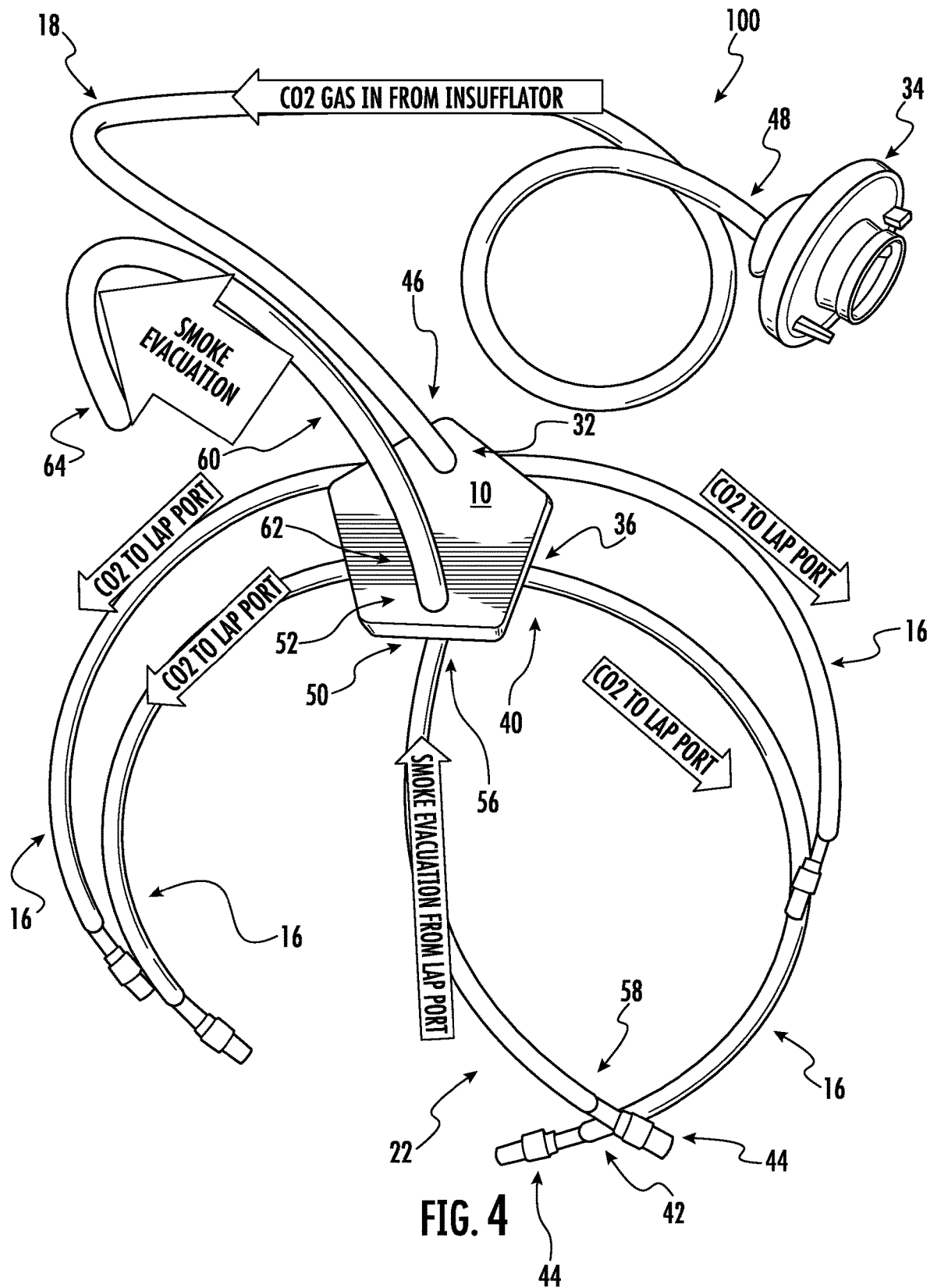
FIG. 4 illustrates an insufflation system according to some embodiments.

FIGS. 3A-3F illustrate additional views of an example embodiment of an insufflation device 10. FIG. 4 illustrates an example of a complete insufflation system 100 according to some embodiments. As described below, other configurations for the distribution device 10, including the number and type of ports, are contemplated. FIG. 3A shows top and bottom sections overlaid. FIG. 3B shows the complementary design of the top and bottom sections. FIG. 3C shows a top view of the top section. FIG. 3D shows the undersurface of the top section as seen from an angle. FIG. 3E shows the undersurface of the top section as seen from a top view. FIG. 3F shows the bottom section.

Referring to FIGS. 1-4, the insufflation system 100 includes the gas flow distribution device 10. The device 10 includes a housing 30 that defines the insufflation chamber 12 and the exhaust chamber 14. The housing 30 may include a bottom or lower portion 30b and a top or upper portion 30t. The bottom portion 30b and the top portion 30t are configured to be coupled or fit together as described in more detail herein. In some other embodiments, the housing 30 is a single piece or monolithic housing.

An insufflation inlet port 32 is on the housing and is configured to be connected to an insufflator 34 via tubing 18. The inlet port 32 may be on the top of the housing 30 such as on the top portion 30t of the housing.

A plurality of insufflation outlet ports 36 are on the housing 30 with each configured to be connected to a dedicated or individual trocar 38. The outlet ports 36 may be on a side of the housing 30 such as on an outer wall 30w of the housing 30 (or the bottom portion 30b of the housing 30). As described herein, the plurality of outlet ports 36 allow for gas to be insufflated in the patient at a higher flow rate as compared to presently used techniques.

As described in more detail below, the inlet port 32 and/or the outlet ports 36 may be configured to receive tubing with a pressure fit. That is, an inner surface of the tubing directly contacts or engages the inlet port or outlet port. This may allow for a larger flow area and increased gas flow as compared to other connections such as a luer lock connection.

In some embodiments, the insufflation system 100 includes tubing that is attached to the inlet port and/or outlet ports (or is configured to be attached to the inlet port and/or outlet ports). For example, with reference to FIG. 4, the system 100 may include insufflation outlet tubing 16 connected to each outlet port 36 (or configured to be connected to each outlet port 36). Each outlet tubing 16 may include a first end 40 and an opposite second end 42. The first end 40 may be connected to the outlet port 36 with a pressure fit as described above. In some embodiments, the second end 42 may include a luer lock fitting 44 for convenient connection to a trocar, as many existing trocars include a luer lock connection.

In some embodiments, the insufflation system 100 may include insufflation inlet tubing 18 connected to the inlet port 32 (or configured to be connected to the inlet port 32). The inlet tubing 18 may include a first end 46 and an opposite second end 48. The first end 46 may be connected to the inlet port 32 with a pressure fit as described above or luer lock connection. The second end 48 may be connected to the insufflator 34.

Still referring to FIGS. 1-4, the housing 30 also defines the exhaust chamber 14. An exhaust inlet port 50 is on the housing 30 and configured to be connected to a trocar 38. The inlet port may be on the outer wall 30w of the housing 30 (or the bottom portion 30b of the housing).

An exhaust outlet port 52 is on the housing 30 and configured to be connected to an exhaust system 54. The outlet port 52 may be on the top of the housing 30 such as on the top portion 30t of the housing.

Referring to FIG. 4, in some embodiments, the system 100 may include exhaust inlet tubing 22 connected to the inlet port 50 (or configured to be connected to the inlet port 50). The inlet tubing 22 may include a first end 56 and an opposite second end 58. The first end 56 may be connected to the inlet port 50 with a pressure fit as described above. In some embodiments, the second end 58 may include a luer lock fitting 44 for convenient connection to a trocar.

In some embodiments, the insufflation system 100 may include exhaust outlet tubing 60 connected to the outlet port 52 (or configured to be connected to the outlet port 52). The outlet tubing 60 may include a first end 62 and an opposite second end 64. The first end 62 may be connected to the outlet port 52 with a pressure fit as described above. The second end 64 may be connected to the exhaust system 54.

The housing 30 includes a partition 66 to isolate the insufflation chamber 12 and the exhaust chamber 14.

Figure 5:
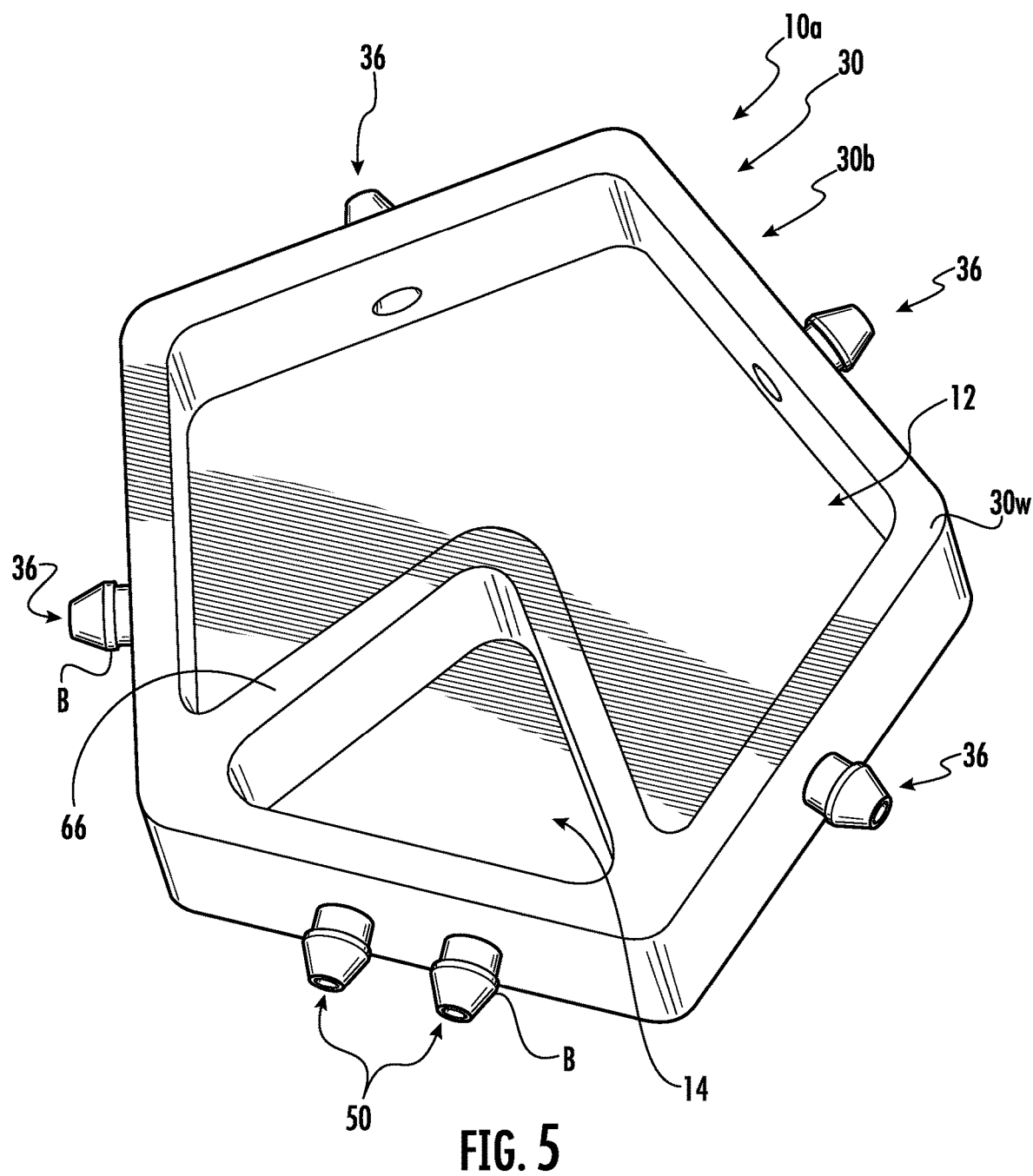
FIG. 5 is a top perspective view of a bottom portion of a housing of a gas flow distribution device according to some embodiments.
Figure 6:
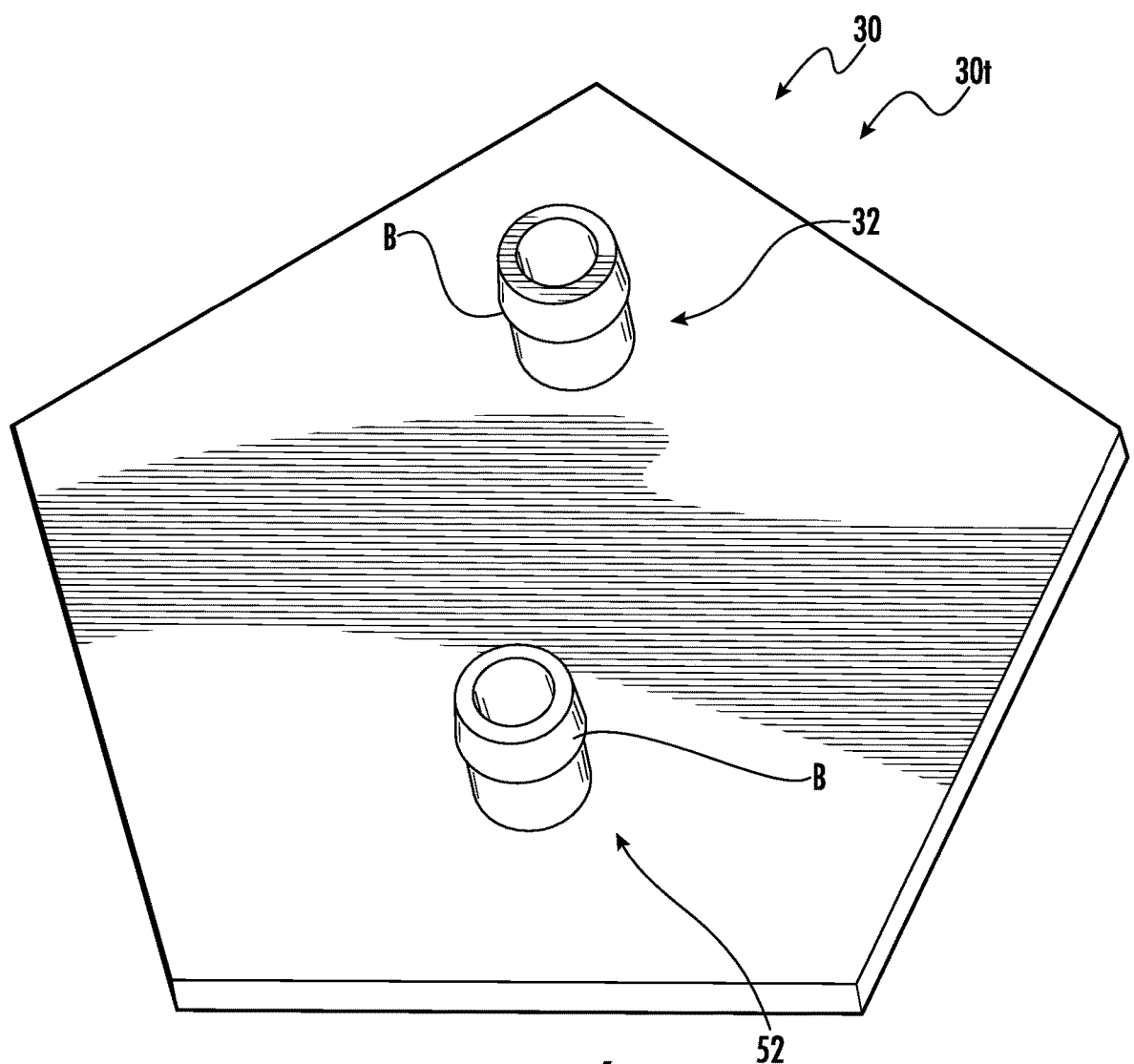
FIG. 6 is a top perspective view of a top portion of the housing of the gas flow distribution device of FIG. 5.
Figure 7:
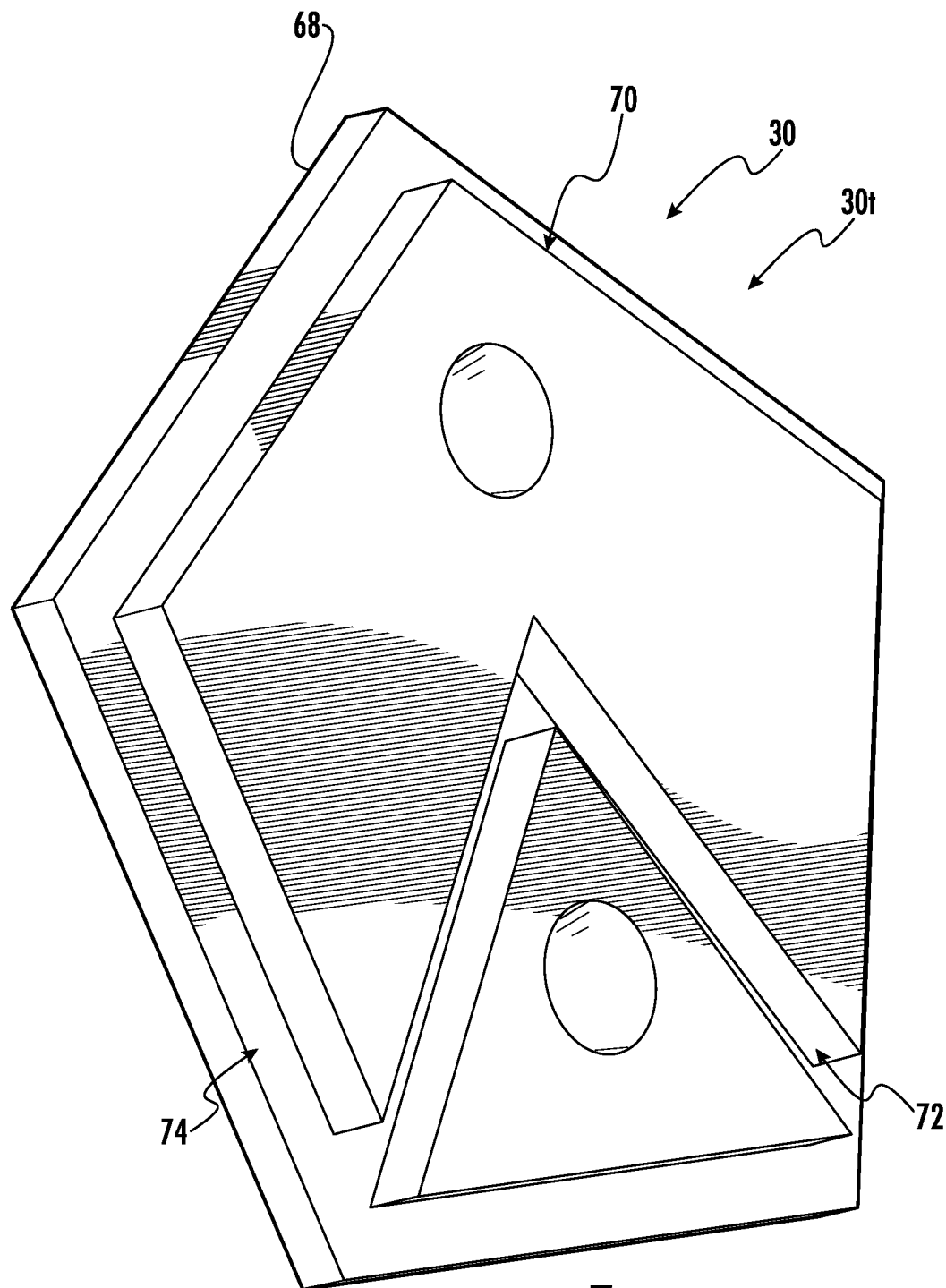
FIG. 7 is a bottom perspective view of the top portion of the housing of FIG. 6.

A gas flow distribution device 10a according to some embodiments is shown in FIGS. 5-7. The device 10a is similar to the device 10 but includes a plurality of exhaust inlet ports 50 (e.g., two exhaust inlet ports 50). The allows for enhanced flow capacity during smoke evacuation or suction. For example, there may be two exhaust trocars with one of the exhaust inlet ports 50 connected to each of the exhaust trocars. There may be a valve (e.g., valve 24 in FIG. 1) in the line or tubing from the smoke evacuation trocar that temporarily turns off the smoke evacuation when suction is activated.

For example, referring to FIG. 1, the system 100 may include a suction device or system 55. A suction line 57 may be placed through one of the trocars 38 to the suction device 55. A suction valve 59 may be in the suction line or tubing 57. In some embodiments, when the suction valve 59 is activated or opened, the smoke evacuation valve 24 is closed (e.g., automatically closed). In some embodiments, as described herein, the valves 24, 59 may be a three way valve with the suction line or tubing 57 and the smoke evacuation line or tubing 60 connected thereto. In this case, the exhaust device 54 and the suction device 55 may be combined.

The embodiment shown in FIGS. 5-7 also more clearly illustrates that the ports 32, 36, 50, 52 may include a barb B. The barb B projects outwardly from the body of the port and engages and retains tubing on the port when the tubing is pressure fit to the port.

FIG. 7 shows an underside of the top portion 30t of the housing 30. The top portion 30t of the housing 30 may include a top wall 68 and a projection 70 extending from the top wall 68. The top wall 68 and the projection 70 may define a central recess 72 and an outer recess 74.

Referring to FIGS. 5 and 7, when the bottom portion 30b of the housing 30 and the top portion 30t of the housing 30 are coupled or fit together, the projection 70 may be received in the chambers 12, 14. In addition, the partition 66 may be received in the central recess 72 and the outer wall 30w may be received in the outer recess 74. In some embodiments, the bottom portion 30b of the housing 30 and the top portion 30t of the housing 30 are coupled together with a friction or interference fit.

In some embodiments, the housing 30 has a polygonal shape. For example, the housing may have a pentagonal shape.

Figure 8:
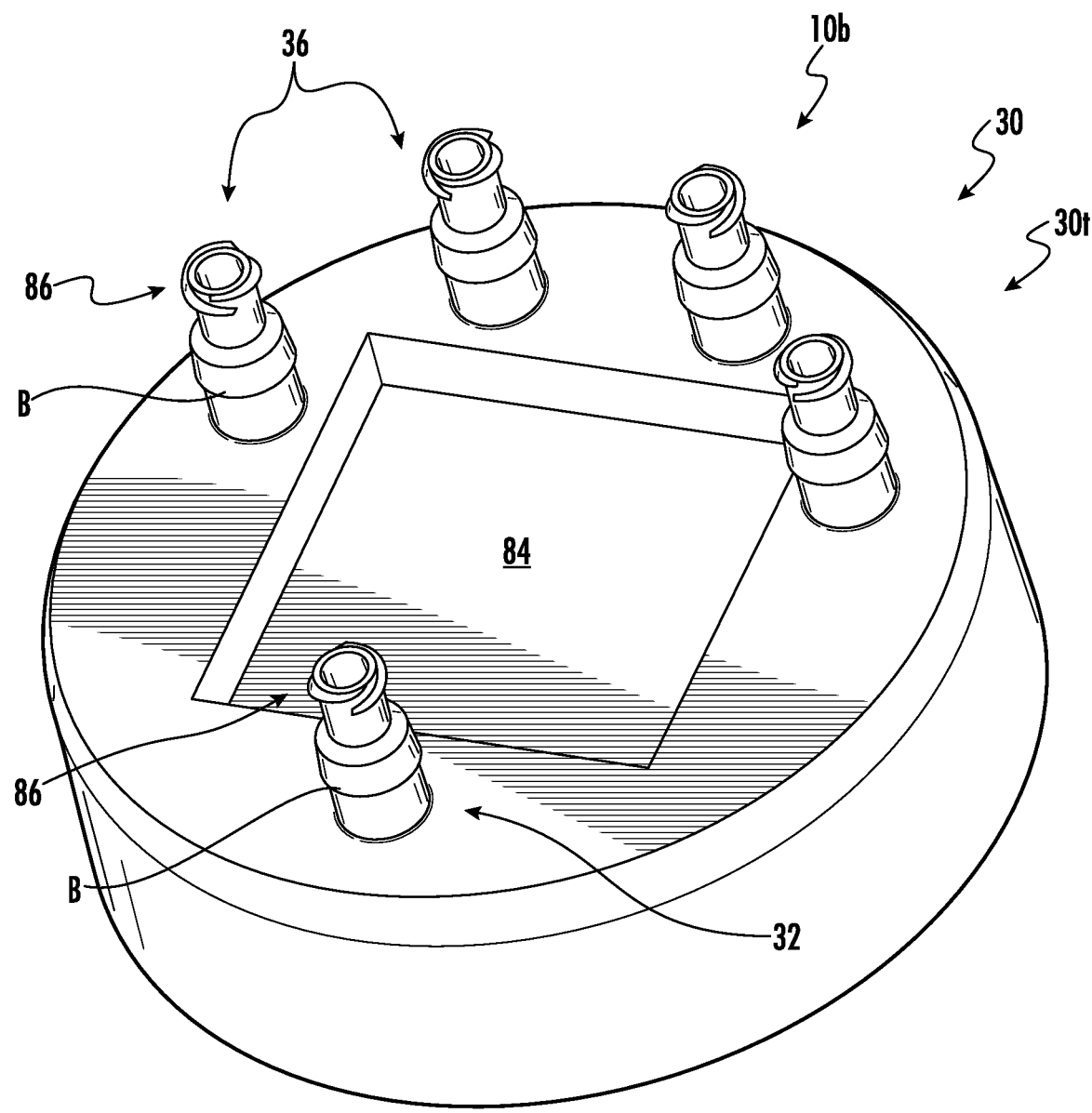
FIG. 8 is a top perspective view of a top portion of a housing of a gas flow distribution device according to some embodiments.
Figure 9:
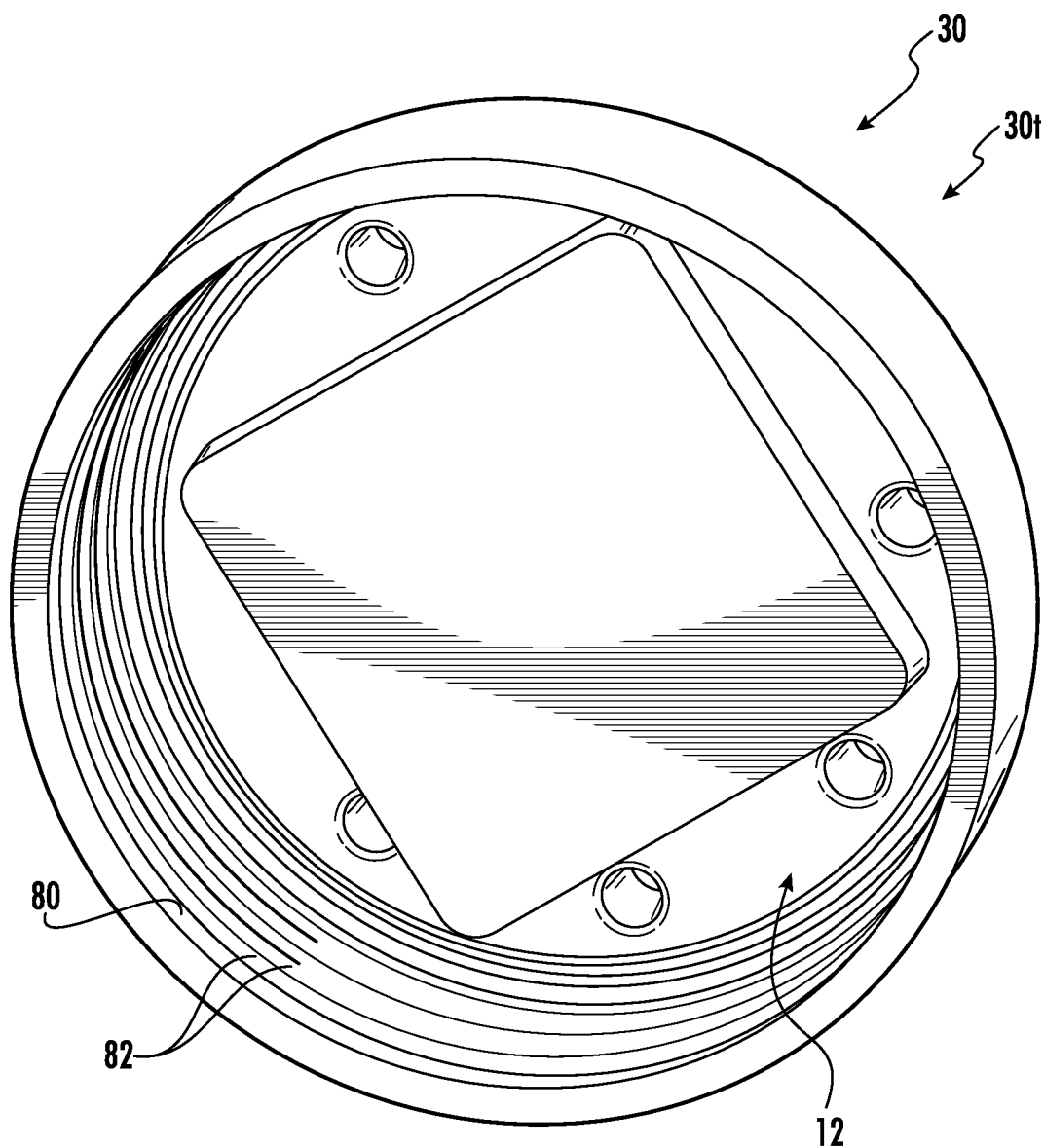
FIG. 9 is a bottom perspective view of the top portion of the housing of FIG. 8.
Figure 10:
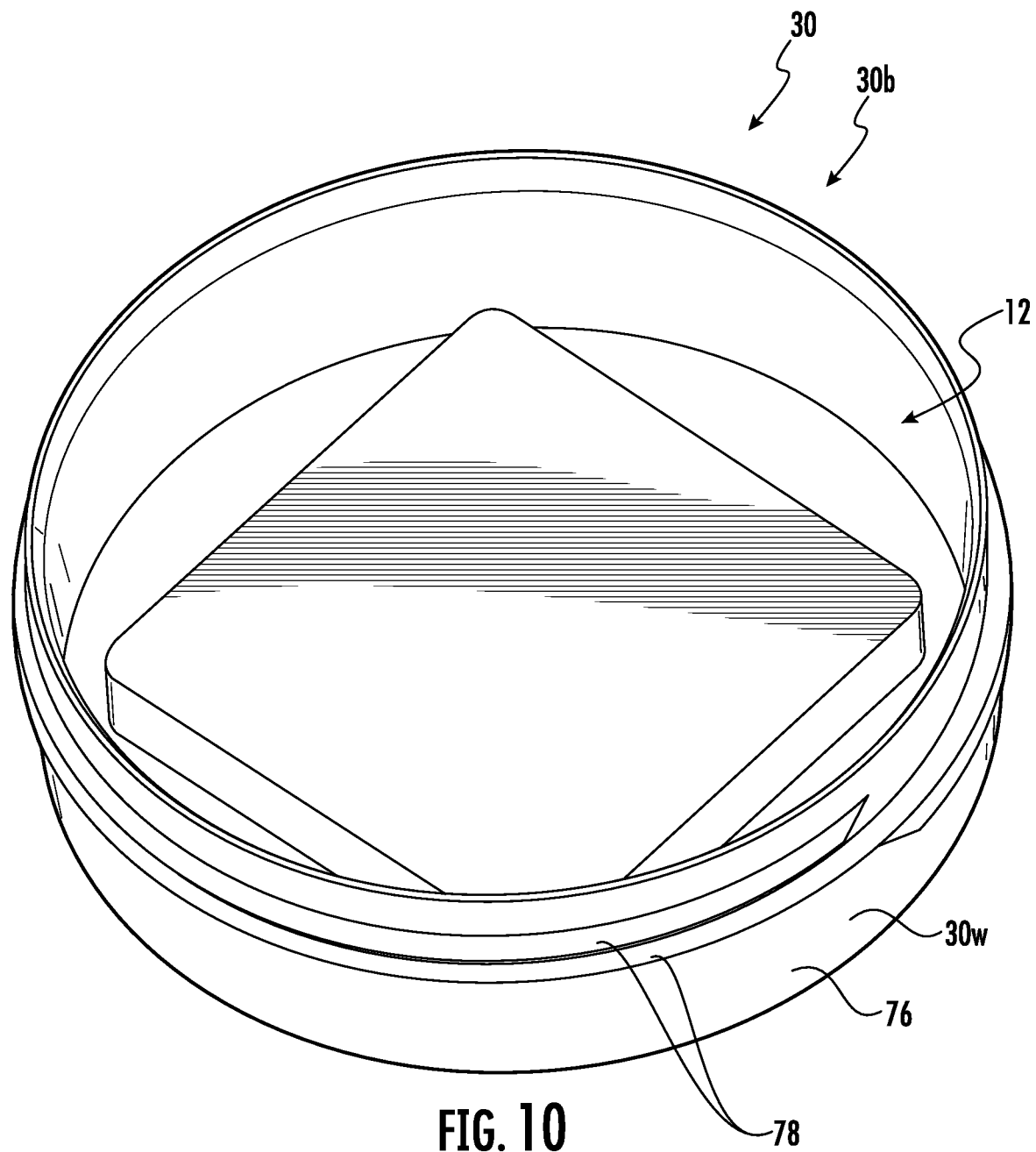
FIG. 10 is a top perspective view of a bottom portion of the housing of the gas flow distribution device of FIG. 8.

In some other embodiments, the housing 30 has a circular shape, such as with the gas flow distribution device 10b shown in FIGS. 8-10. The housing 30 may include a lower or bottom portion 30b and an upper or top portion 30t that define an insufflation chamber 12. An insufflation inlet port 32 and a plurality of insufflation outlet ports 36 are on the housing 30. In some embodiments, the inlet port 32 and the plurality of outlet ports 36 are on the top portion 30t of the housing 30.

Referring to FIGS. 9 and 10, the bottom portion 30b and the top portion 30t of the housing 30 are configured to threadingly engage one another. For example, the bottom portion 30b (or the outer wall 30w thereof) may include an outer surface 76 with threads 78 thereon. The top portion 30t (or the outer wall 30w thereof) may include an inner surface 80 with threads thereon 82. The bottom portion 30b and the top portion 30t of the housing 30 can be coupled together by rotating one relative to the other such that the threads 78, 82 engage.

An inset or reservoir 84 may be on the top of the housing 30. The reservoir 84 may be used to hold a sponge filled with a surfactant to reduce fogging on a laparoscopic lens. Such sponges are typically attached to drapes with adhesive but the reservoir 84 provides a convenient central location for the sponge. Alternatively, raised 90 degree projections can be used to define the four corners of the square configured to hold the sponge.

In some embodiments, the reservoir 84 can be heated (e.g., the device 10 may include an internal heater in the housing 30). The reservoir 84 may be used for warming both the surfactant sponge to help warm the camera and prevent fogging and the insufflation gas (e.g., $CO_2$ gas). There are presently various in-line warming options for the gas but none seem to do an adequate job of providing warm $CO_2$. Maintaining patient body temperature throughout surgery is an important quality measure and has been shown to reduce postoperative complications.

The inlet port 32 and/or the outlet ports 36 may include a luer lock connection 86 and a barb B to allow a user to either connect tubing with a luer lock fitting or to directly connect the tubing to the port using a pressure fit with the tubing directly contacting the barb B. This provides flexibility for the user but, as described herein, it may be preferable to use the barb B for a pressure fit to provide a larger flow area and higher gas flow rate.

Figure 11:
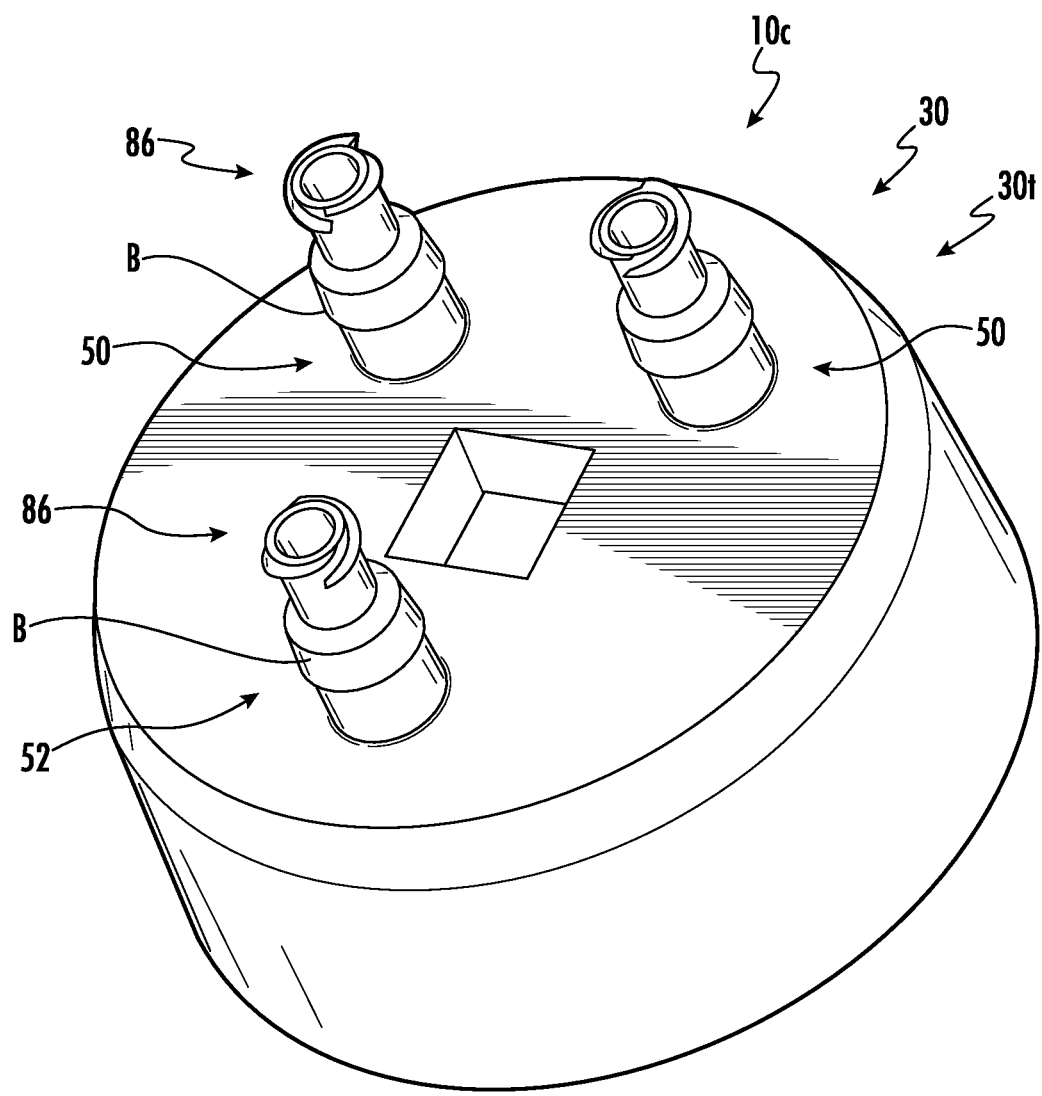
FIG. 11 is a top perspective view of a top portion of a housing of a gas flow distribution device according to some embodiments.
Figure 12:
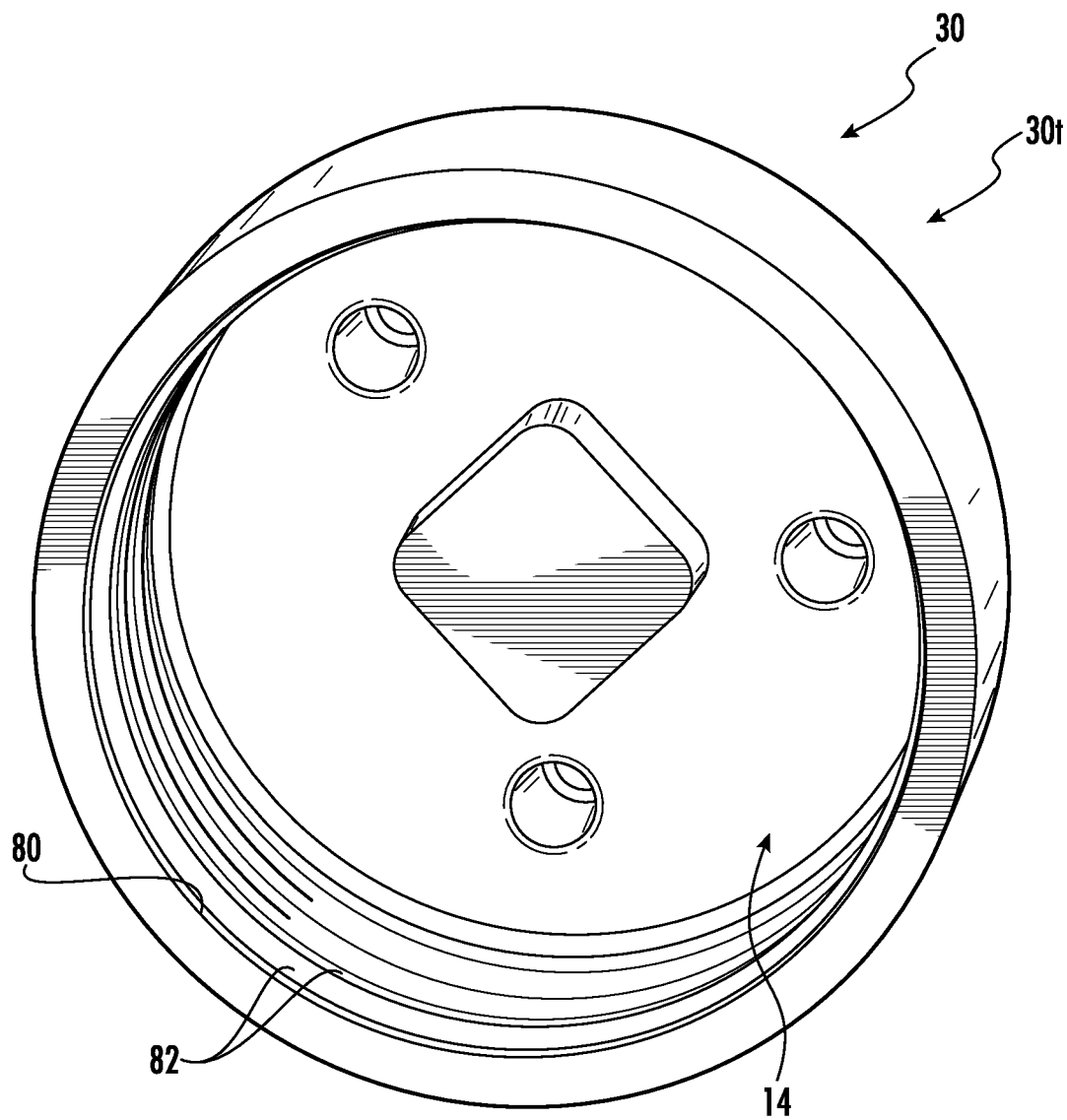
FIG. 12 is a bottom perspective view of the top portion of the housing of FIG. 11.
Figure 13:
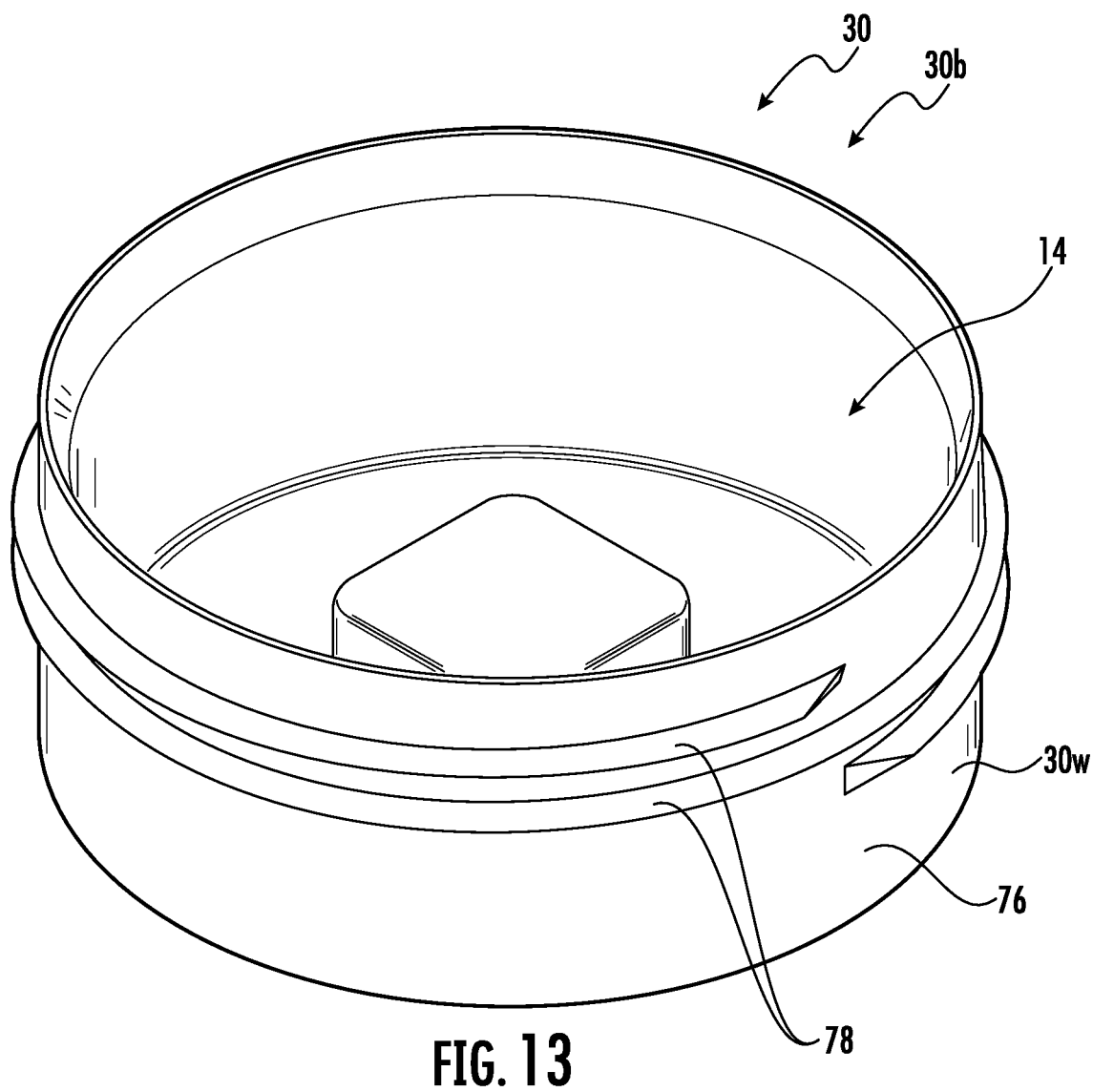
FIG. 13 is a top perspective view of a bottom portion of the housing of the gas flow distribution device of FIG. 11.

A gas flow distribution device 10c according to some embodiments is shown in FIGS. 11-13. The device 10c may be similar to the device 10b but the housing 30 may be smaller and define an exhaust chamber 14. At least one exhaust inlet port 50 and an exhaust outlet port 52 are on the housing 30. In some embodiments, the inlet port(s) 50 and outlet port 52 are on the top portion 30t of the housing 30. In the illustrated embodiment, a plurality (e.g., two) of inlet ports 50 are provided.

The housing 30 may include a bottom portion 30b and a top portion 30t that can be threadingly engaged as described above with regard to the device 10b.

The housing 30 may include a reservoir 84 to hold a sponge with surfactant as described above with regard to the device 10b.

The inlet port(s) 50 and/or the outlet port 52 may include a luer lock connection 86 and a barb B to provide flexibility as described above.

The device 10c may be used with the device 10b described above to provide an insufflation and exhaust system.

A gas flow distribution device 10d according to some embodiments is illustrated in FIGS. 14-17. The device 10d includes a housing 30 that may include a bottom portion 30b and a top portion 30t.

An insufflation inlet port 32 is on the housing 30. The inlet port 32 may be on the top of the housing 30 such as on the top portion 30t of the housing. A plurality of insufflation outlet ports 36 are on the housing 30. The outlet ports 36 may be on a side of the housing such as on an outer wall 30w of the housing 30 (or the bottom portion 30b of the housing).

An exhaust inlet port 50 is on the housing 30. The inlet port 50 may be on the outer wall 30w of the housing 30 (or the bottom portion 30b of the housing). An exhaust outlet port 52 is on the housing 30. The outlet port 52 may be on the top of the housing 30 such as on the top portion 30t of the housing.

A flex port 88 is on the housing 30. The flex port 88 may be on the outer wall 30w of the housing 30 (or the bottom portion 30b of the housing). The flex port 88 may be between the exhaust inlet port 50 and one of the insufflation outlet ports 36.

The housing 30 includes a partition 66 to isolate the insufflation chamber 12 and the exhaust chamber 14. The partition 66 includes a central hub or post 90 and a stationary panel 92 that extends between the post 90 and the outer wall 30w of the housing 30. The partition 66 includes an adjustable or movable insert 94 (FIG. 17A).

Figure 14:
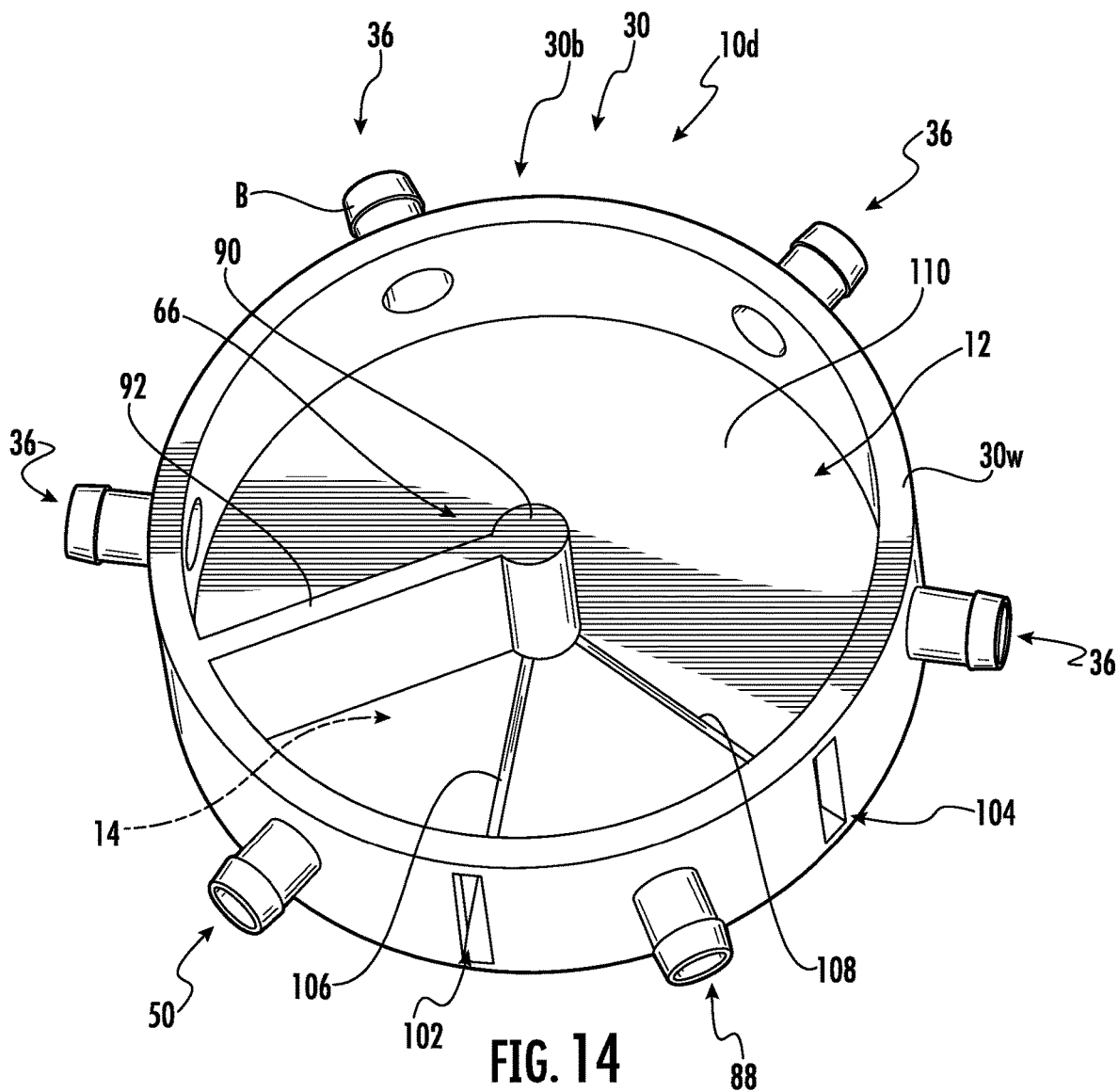
FIG. 14 is a top perspective view of a bottom portion of a housing of a gas flow distribution device according to some embodiments.
Figure 15:
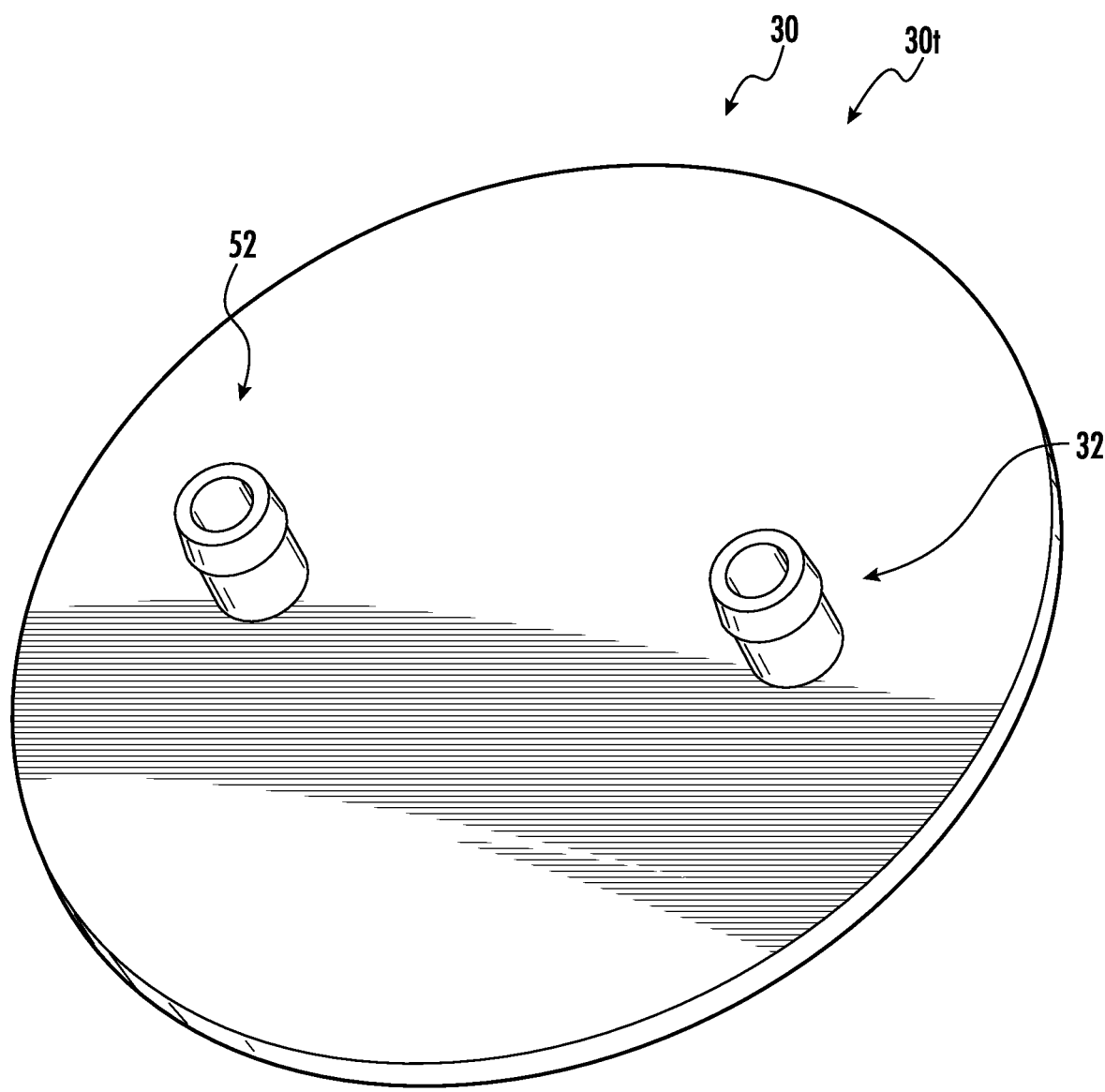
FIG. 15 is a top perspective view of a top portion of the housing of the gas flow distribution device of FIG. 14.

Referring to FIG. 14, the housing 30 includes first and second slots 102, 104. The slots 102, 104 may be defined in the outer wall 30w of the housing 30 (or the bottom portion 30b of the housing 30). The flex port 88 may be between the first slot 102 and the second slot 104.

There may be first and second channels 106, 108 in a bottom wall 110 of the housing 30. The first channel 106 may extend between the first slot 102 and the post 90 and the second channel 108 may extend between the second slot 104 and the post 90.

Figure 17A:
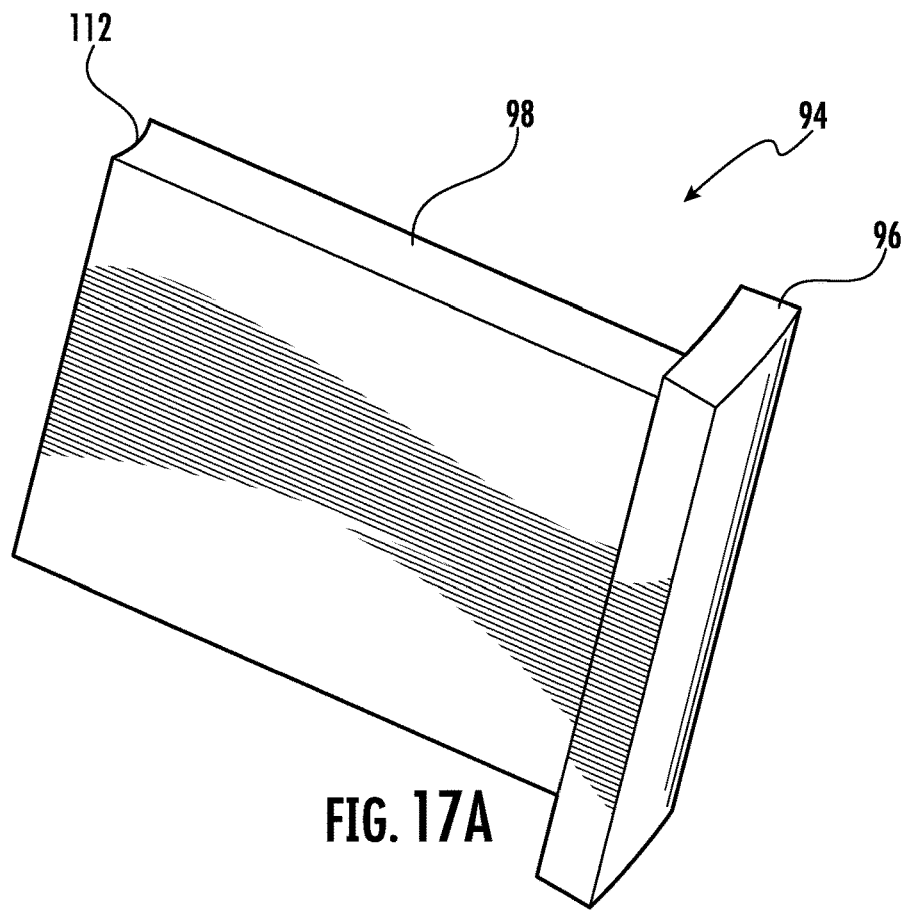
FIG. 17A is a perspective view of a partition insert configured for use with the housing of FIG. 14.

Referring to FIGS. 14 and 17A, the insert 94 includes a base 96 and a panel 98. A user may selectively insert the insert 94 through either the first slot 102 or the second slot 104. The base 96 covers the selected slot and the panel 98 is held in either the first channel 106 or the second channel 108. The panel 98 extends from the selected slot to the post 90. A distal end of the panel 98 may include a curved surface 112 (e.g., concave surface) to fit against the correspondingly curved post 90.

A user can select between the first slot 102 or the second slot 104 for the insert 94 to select a size of the exhaust chamber 14 and the number of exhaust inlet ports 50. The user can select the first slot 102 for the insert 94 to provide a smaller exhaust chamber 14 and a single exhaust inlet port 50. The flex port 88 is then in fluid communication with the insufflation chamber 12 and can be used as an additional insufflation outlet port 36 if desired.

The user can select the second slot 104 for the insert 94 to provide a larger exhaust chamber 14 and a two exhaust inlet ports 50. The flex port 88 is then in fluid communication with the exhaust chamber 14 and can be used as the second exhaust inlet port 50.

Figure 17B:
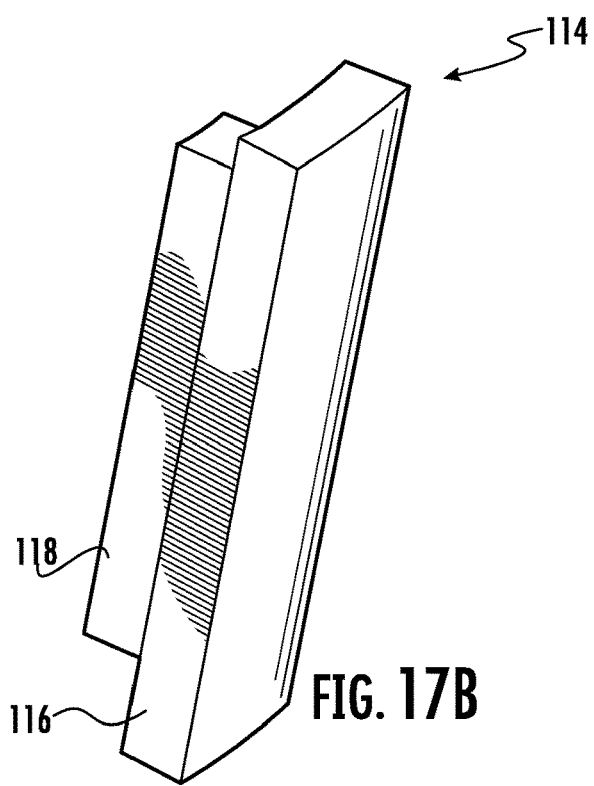
FIG. 17B is a perspective view of a plug insert configured for use with the housing of FIG. 14.

Referring to FIGS. 14 and 17B, a plug insert 114 can be inserted into the unselected one of the first and second slots 102, 104 to provide an airtight chamber. The insert 114 includes a base 116 and a plug 118. The base 116 is configured to cover the slot and the plug 118 is configured to be received in the slot.

Figure 16:
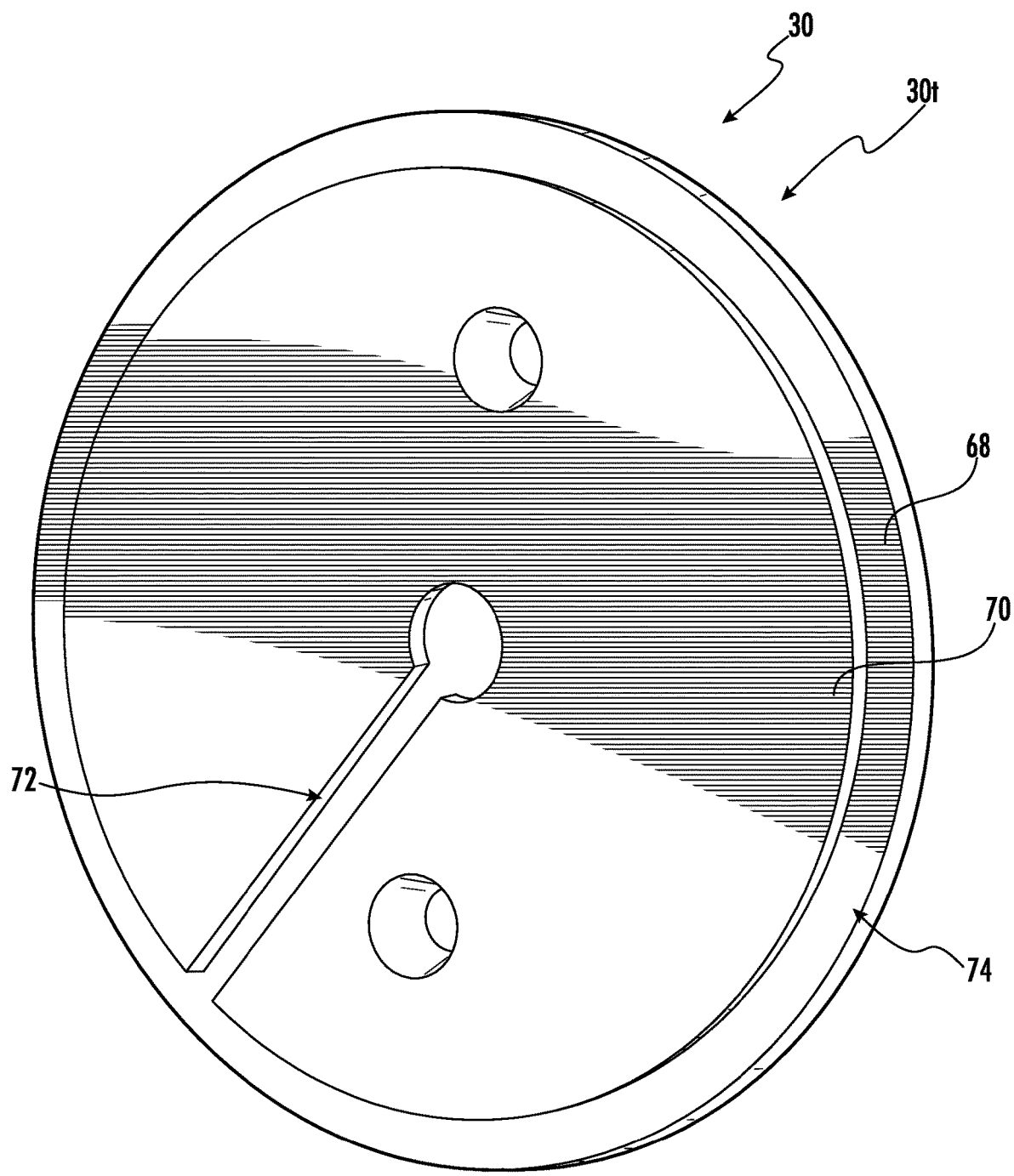
FIG. 16 is a bottom perspective view of the top portion of the housing of FIG. 15.

FIG. 16 shows an underside of the top portion 30t of the housing 30. The top portion 30t of the housing 30 may include a top wall 68 and a projection 70 extending from the top wall 68. The top wall 68 and the projection 70 may define a central recess 72 and an outer recess 74.

Referring to FIGS. 14 and 16, when the bottom portion 30b of the housing 30 and the top portion 30t of the housing 30 are coupled or fit together, the projection 70 may be received in the chambers 12, 14. In addition, the partition 66 (e.g., the post 90 and the panel 92) may be received in the central recess 72 and the outer wall 30w may be received in the outer recess 74. In some embodiments, the bottom portion 30b of the housing 30 and the top portion 30t of the housing 30 are coupled together with a friction or interference fit.

Figure 18:
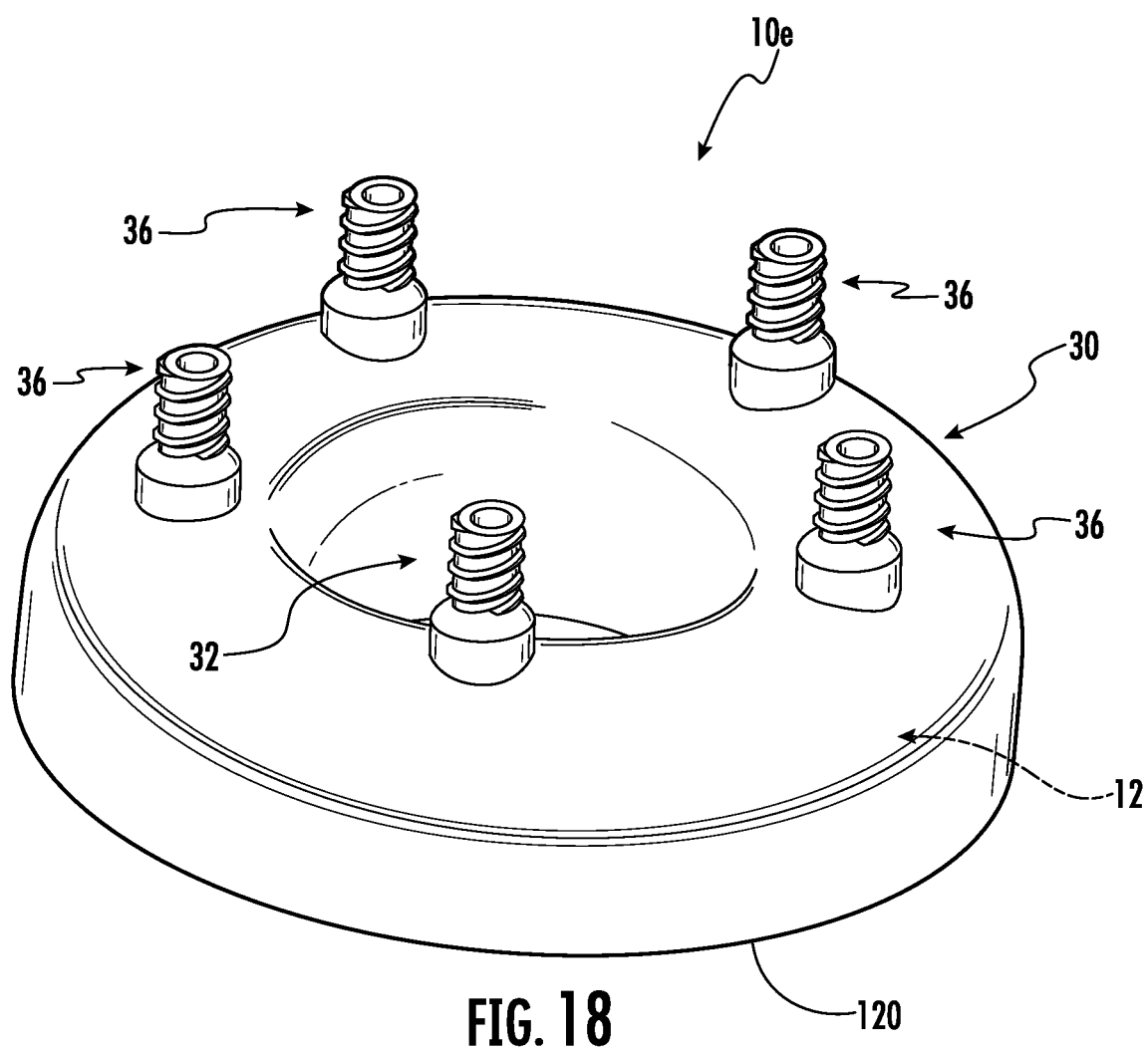
FIG. 18 is a top perspective view of a gas flow distribution device according to some embodiments.

Other housing shapes are contemplated. For example, referring to FIG. 18, a gas flow distribution device 10e includes a housing 30 that may have a toroidal shape optionally with a flat bottom surface 120. An insufflation inlet port 32 and a plurality of insufflation outlet ports 36 may be on the housing 30. The truncated donut shaped housing 30 may define the insufflation chamber 12.

Figure 19:
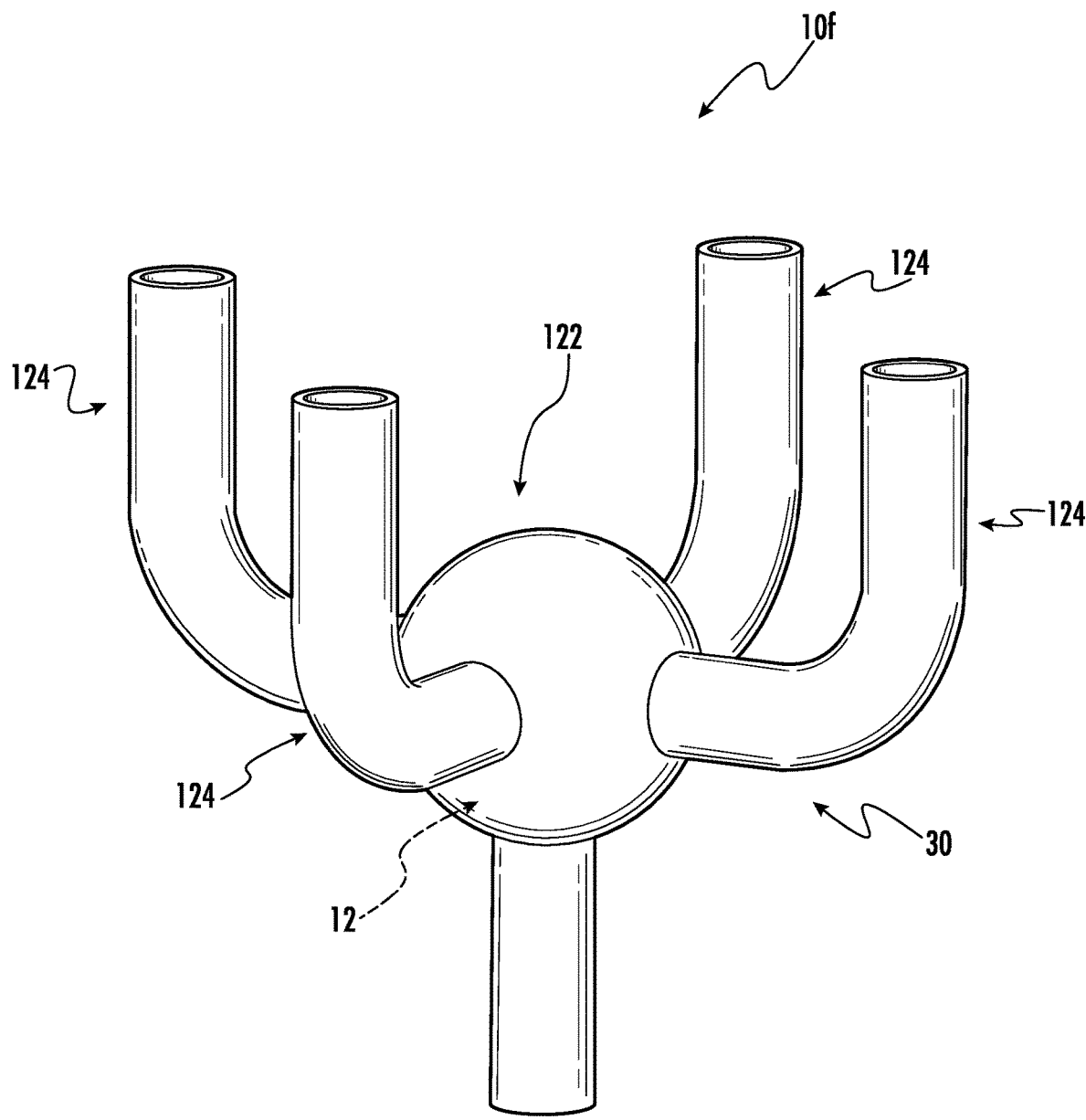
FIG. 19 is a perspective view of a gas flow distribution device according to some embodiments.

Referring to FIG. 19, a gas flow distribution device 10f includes a housing 30 that may have a central spherical body portion 122. A plurality of legs 124 may extend from various sides of the spherical portion 122. The legs 124 may define the insufflation inlet port 32 and the plurality of insufflation outlet ports 36. The spherical portion 122 may define the insufflation chamber 12.

Figure 20:
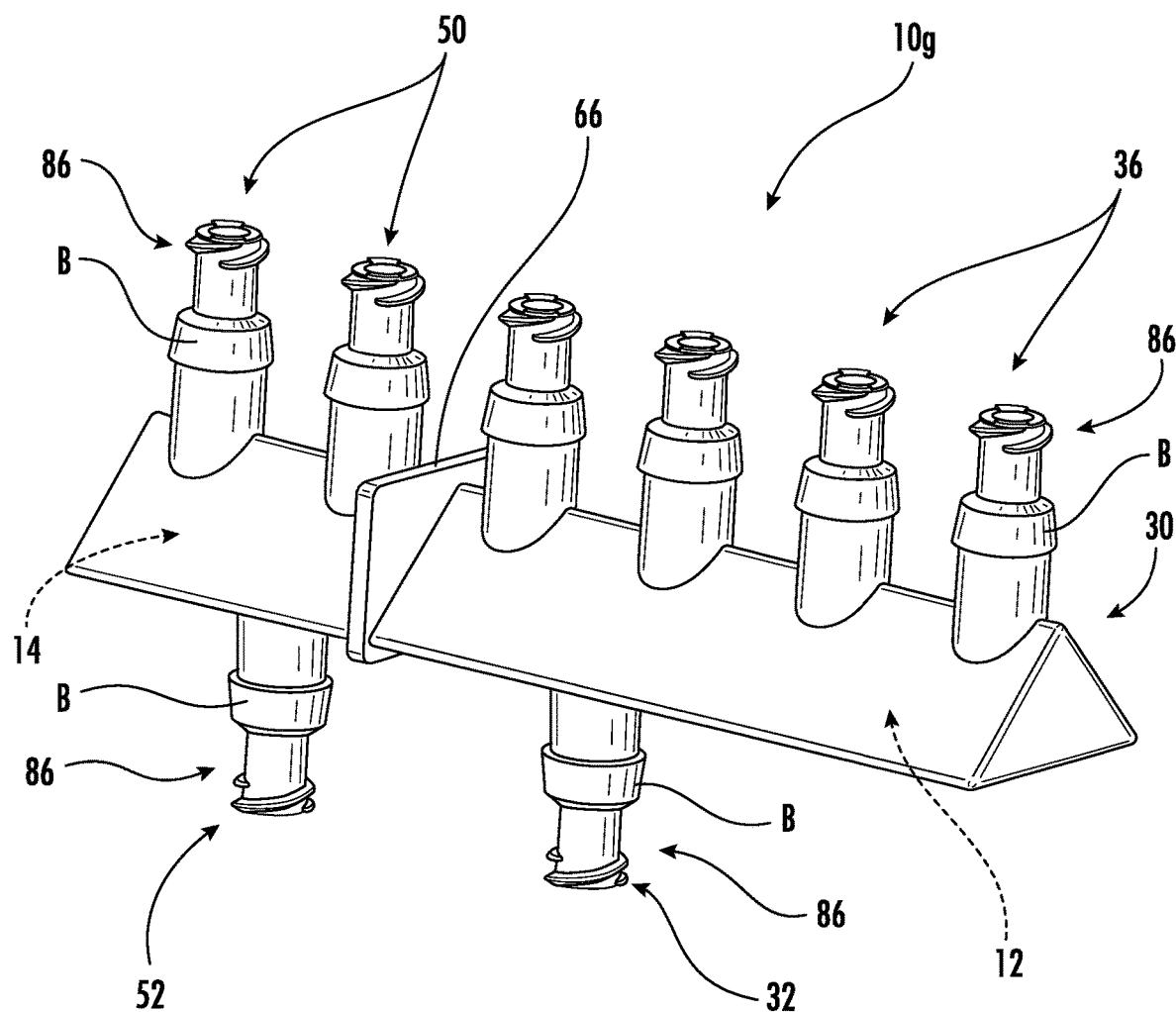
FIG. 20 is a perspective view of a gas flow distribution device according to some embodiments.

Referring to FIG. 20, a gas flow distribution device 10g includes a housing 30 that may include an in-line insufflation chamber 12 and exhaust chamber 14 with a partition 66 fluidly isolating the insufflation chamber 12 and exhaust chamber 14. The housing 30 may have an elongated triangular profile. The insufflation inlet port 32 and the smoke evacuation outlet port 52 may be on a bottom portion of the housing 30 (e.g., a flat planar surface of the triangular housing). The insufflation outlet ports 36 and the smoke evacuation inlet port(s) 50 may be on a top portion of the housing 30 (e.g., an apex of the housing). The ports may include barbs and/or luer connections as described above.

The gas flow distribution devices 10b, 10c, 10d, 10e, 10f, and 10g may be formed of any suitable material. In some embodiments, the devices are formed of a polymer.

The gas flow distribution devices 10b, 10c, 10d, 10e, 10f, and 10g (and any tubing and/or fittings) connected thereto may be single use disposable. In some embodiments and as described above, the device may include a two piece housing that may be opened to facilitate cleaning and/or sterilization.

Any of the gas flow distribution devices 10b, 10c, 10d, 10e, 10f, and 10g (alone or in combination) may be used with the insufflation system 100 of FIG. 4.

With the foregoing features, the disclosed devices and systems overcome several limitations of conventional solutions. For example, the gas supply flow can be higher and more stable compared to a single, one-channel standard trocar. Insufflation system 100 can increase insufflation inflow capacity 2-4X over conventional systems. Additionally, the disclosed system can be adapted to work with any existing insufflation system, thus eliminating the need to use supplier-specific equipment. Currently, insufflation systems are configured to require brand unity for every element of the system. The devices and systems described herein can potentially reduce the cost and complexity of laparoscopic surgery, while increasing flexibility, through the ability to blend differing systems. Further, it is not necessary to use oversized trocars, thus reducing patient impact.

Another embodiment of the present disclosure provides a method of insufflating a subject using insufflation system 100.

Another aspect of the present disclosure provides all that is described and illustrated herein.

The term "pneumoperitoneum" has been used herein in relation to insufflation of the abdominal cavity. However, one skilled in the art will also appreciate that the devices and systems described herein can also be used for artificial pneumothorax or creation of positive pressure artificial cavity for use in the thoracic or other cavities.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

We claim:

1. An insufflation system for creating a high-flow, constant or variable pressure pneumoperitoneum, the system comprising:
a gas flow distribution device comprising:
a single-piece housing defining an insufflation chamber;
a single inlet port on the housing in direct fluid communication with the insufflation chamber without any intervening components therebetween, the inlet port configured to be connected to an insufflator to provide pressurized insufflation gas from the insufflator to the insufflation chamber, the inlet port extending outwardly away from the housing; and
a plurality of outlet ports on the housing in direct fluid communication with the insufflation chamber without any intervening components therebetween, the plurality of outlet ports configured to be connected to a plurality of insufflation trocars inserted in a single cavity of a patient, each outlet port configured to be connected to a dedicated one of the plurality of insufflation trocars, to concurrently distribute the pressurized insufflation gas from the insufflation chamber to each of the plurality of insufflation trocars and into the single cavity, each outlet port extending outwardly away from the housing,
wherein, with the exception of the inlet port and the plurality of outlet ports, the housing is free of any openings in fluid communication with the insufflation chamber, and
wherein the housing further defines an exhaust chamber, the insufflation system further comprising:
at least one exhaust inlet port on the housing and configured to be connected to an exhaust trocar to provide suction and/or evacuate smoke from the exhaust trocar to the exhaust chamber; and
an exhaust outlet port on the housing and configured to be connected to an exhaust device to provide exhaust from the exhaust chamber to the exhaust device.

2. The insufflation system of claim 1 wherein the inlet port comprises a barb configured to directly engage an inner surface of tubing connected thereto.

3. The insufflation system of claim 2 wherein the inlet port comprises a luer lock connection configured to receive a luer lock fitting.

4. The insufflation system of claim 1 wherein each outlet port comprises a barb configured to directly engage an inner surface of tubing connected thereto.

5. The insufflation system of claim 4 wherein each outlet port comprises a luer lock connection configured to receive a luer lock fitting.

6. The insufflation system of claim 4 further comprising a plurality of outlet tubes, each outlet tube comprising a first end and a second opposite end, the first end of each outlet tube configured to be connected to a corresponding one of the outlet ports, the second end of each outlet tube configured to be connected to the dedicated trocar.

7. The insufflation system of claim 6 wherein the first end of each outlet tube is pressure fit to a corresponding one of the outlet ports such that an inner surface of the outlet tube directly engages the barb on an outer surface of the outlet port.

8. The insufflation system of claim 6 further comprising a luer lock fitting at the second end of each of the outlet tubes.

9. The insufflation system of claim 1 further comprising a reservoir in a top of the housing that is sized and configured to receive and hold a sponge comprising surfactant to reduce fogging on a laparoscopic lens.

10. The insufflation system of claim 9, wherein the inlet port and the plurality of outlet ports are on the top of the housing and surround the reservoir.

11. The insufflation system of claim 1 wherein the housing includes a partition that isolates the insufflation chamber and the exhaust chamber from one another.

12. The insufflation system of claim 1 further comprising a partition that isolates the insufflation chamber and the exhaust chamber from one another, wherein the partition comprises an insert configured to be received through at least one slot in a side wall of the housing.

13. The insufflation system of claim 12 wherein the at least one slot comprises first and second slots, the device further comprises a flex port between the first and second slots, and the insert is configured to selectively be received (i) through the first slot such that the exhaust outlet port is in fluid communication with the exhaust chamber and the flex port is in fluid communication with the insufflation chamber and (ii) through the second slot such that the exhaust outlet port and the flex port are in fluid communication with the exhaust chamber.

14. The insufflation system of claim 13 wherein the insert is a first insert, the insufflation system further comprising a second insert configured to be received in and plug the first or second slot that is not holding the first insert.

15. The insufflation system of claim 1 further comprising at least one inlet tube each comprising a first end and a second opposite end, the first end of each inlet tube configured to be connected to a corresponding one of the at least one exhaust inlet port, the second end of each inlet tube configured to be connected to a dedicated exhaust trocar.

16. The insufflation system of claim 15 wherein the first end of each inlet tube is pressure fit to a corresponding one of the at least one exhaust inlet port such that an inner diameter of the inlet tube directly engages a barb on an outer surface of the exhaust inlet port.

17. The insufflation system of claim 16 further comprising a luer lock fitting at the second end of each inlet tube.

18. The insufflation system of claim 1 further comprising a suction system comprising a suction line configured to connect (i) at least one of the plurality of insufflation trocars or the exhaust trocar to (ii) the exhaust device or a separate suction device, the system further comprising at least one valve in the suction line configured to close a smoke evacuation line comprising the exhaust outlet port when the at least one valve is open to the exhaust device or the separate suction device, and to open the smoke evacuation line when the at least one valve is closed to the exhaust device or the separate suction device.

19. The insufflation system of claim 1 further comprising the plurality of insufflation trocars configured to be inserted in a single cavity of a patient.

20. The insufflation system of claim 1 wherein the inlet port is integrally formed with the housing.

21. The insufflation system of claim 1 wherein each outlet port is integrally formed with the housing.

22. A method for creating a high-flow, constant or variable pressure pneumoperitoneum, the method comprising:
inducing a pneumoperitoneum in a patient comprising:
providing the gas flow distribution device of claim 1;
flowing gas from the insufflator through the single inlet port and into the insufflation chamber; and
flowing the gas from the insufflation chamber concurrently through each of the plurality of outlet ports to the plurality of trocars in the single cavity of the patient, wherein each of the plurality of outlet ports is fluidly connected to a dedicated one of the plurality of trocars.

23. The method of claim 22 further comprising, before inducing the pneumoperitoneum in the patient, for each of the plurality of outlet ports, connecting a first end of an outlet tube to an outlet port and connecting a second end of the outlet tube to the dedicated one of the plurality of trocars.

24. The method of claim 23 wherein connecting the second end of the outlet tube to the dedicated one of the plurality of trocars comprises connecting the second end of the outlet tube to the dedicated one of the plurality of trocars using a luer lock connection.

25. The method of claim 23 wherein connecting a first end of an outlet tube to the outlet port comprises connecting the first end of the outlet tube to the outlet port using a pressure fit such that an inner surface of the outlet tube directly engages a barb on the outlet port.

26. The method of claim 22 further comprising, before inducing a pneumoperitoneum in a patient, connecting an inlet tube extending from the insufflator to the inlet port using a pressure fit such that an inner surface of the inlet tube directly engages a barb on the inlet port.

27. The method of claim 22 further comprising evacuating smoke from an abdomen of the patient while inducing the pneumoperitoneum in the patient.

28. The method of claim 27 wherein evacuating smoke from the abdomen of the patient comprises:
flowing smoke from the exhaust trocar through the at least one exhaust inlet port and into the exhaust chamber; and
flowing the smoke from the exhaust chamber through the exhaust outlet port and to the exhaust device.

29. The method of claim 28 wherein the at least one exhaust inlet port comprises first and second exhaust inlet ports, and wherein evacuating smoke from the abdomen of the patient comprises:
flowing first smoke from a first exhaust trocar through the first exhaust inlet port and into the exhaust chamber;
concurrently with flowing the first smoke, flowing second smoke from a second exhaust trocar through the second exhaust inlet port and into the exhaust chamber; and
flowing the first and second smoke from the exhaust chamber through the exhaust outlet port and to the exhaust device.

30. The method of claim 27 further comprising suctioning fluid from the abdomen of the patient.

31. The method of claim 30 further comprising halting evacuating smoke from the abdomen of the patient before suctioning fluid from the abdomen of the patient, and resuming evacuating smoke from the abdomen of the patient after suctioning fluid from the abdomen of the patient.

32. The method of claim 31 wherein halting evacuating smoke from the abdomen of the patient comprises closing at least one valve in a smoke evacuation line in response to opening at least one valve in a suction line, and wherein resuming evacuating smoke from the abdomen of the patient comprises opening at least one valve in the smoke evacuation line in response to closing at least one valve in the suction line.

* * * * *